United States Patent [19]

Yajima et al.

[11] Patent Number: 4,862,873
[45] Date of Patent: Sep. 5, 1989

[54] STEREO ENDOSCOPE

[75] Inventors: Akihiko Yajima, Kunitachi; Tetsuo Nonami, Hachioji; Masahiko Sasaki, Hachioji; Masao Uehara, Hachioji; Takashi Tsukaya, Hachioji; Kenichi Kikuchi, Hachioji; Hiroki Hibino, Hachioji; Takao Tsuruoka, Hachioji; Hiromasa Suzuki, Akishima, all of Japan

[73] Assignee: Olympus Optical Co., Ltd., Tokyo, Japan

[21] Appl. No.: 199,212

[22] Filed: May 26, 1988

[30] Foreign Application Priority Data

May 27, 1987 [JP] Japan .................................. 62-130363

[51] Int. Cl.⁴ .............................................. A61B 1/06
[52] U.S. Cl. ...................... 128/6; 350/96.26; 350/516; 358/98
[58] Field of Search ...................... 128/3, 4, 5, 6, 7, 8; 358/98; 350/515, 516, 517, 96.19, 96.26

[56] References Cited

U.S. PATENT DOCUMENTS 3,520,587 7/1970 Tasaki et al. .................... 350/515
4,061,135 12/1977 Widran et al. .................... 128/6
4,651,201 3/1987 Schoolman ...................... 358/98
4,702,571 10/1987 Barber .............................. 350/516

FOREIGN PATENT DOCUMENTS 55-110208 8/1980 Japan .
57-069839 4/1982 Japan .
61-020488 6/1986 Japan .

Primary Examiner—William H. Grieb
Attorney, Agent, or Firm—Armstrong, Nikaido, Marmelstein, Kubovcik & Murray

[57] ABSTRACT

An apparatus is disclosed which includes a first and a second optical guides inserted in an elongated insertion portion thereof, and which can transmit an optical image, and an optical system with a function of imaging at the end surface of the optical guide. By transmitting an illuminating light from the other end surface to the portion to be observed through one of the optical guides, the portion to be observed is illuminated. While, the optical image transmitted through the other optical guide is introduced into an ocular system or an imaging system. By changing the functions performed by these optical guides, the stereoscopic observation and stereoscopic imaging can be realized.

57 Claims, 21 Drawing Sheets

FIG.2
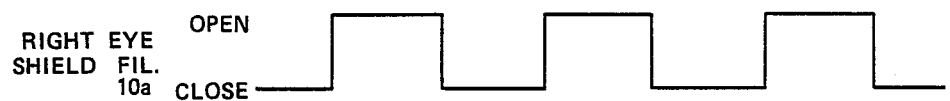
RIGHT EYE SHIELD FIL. 10a   OPEN / CLOSE
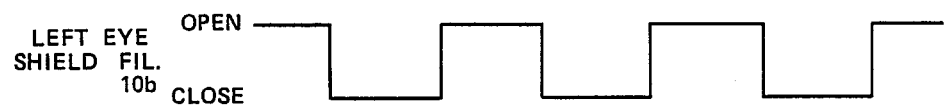
LEFT EYE SHIELD FIL. 10b   OPEN / CLOSE
COLOR CRT
| IMAGE MEMORY 28a | IMAGE MEMORY 28b | IMAGE MEMORY 28a | IMAGE MEMORY 28b | IMAGE MEMORY 28a |
|---|---|---|---|---|
| A FIELD | B FIELD | | | |

FIG.11a FIG.11b

STEREO ENDOSCOPE

BACKGROUND OF THE INVENTION

Industrial Field of the Invention and Description of the Related Art

This invention relates to a stereo endoscope apparatus which is able to stereoscopically observe the portion to be observed.

Recently, endoscopes have been widely used for observing the coelom, internal organs and so forth. In use, an elongated insertion portion thereof is inserted into the coelom or the inner parts of internal organs to observe the coelom or the internal organs, or various types of medical treatment to be performed with the aid, if necessary, of a treatment tool that is inserted into the treatment tool channel thereof, or to observe or treat the inside portion of various mechanical devices.

However, the conventional endoscope can only observe the item to be observed, for example, a coelom, in the form of a planar object, without perspective. It therefore involves a problem in that, for example, it is difficult to observe any slight unevenness on the surface of a coelom, which is a very important factor as a diagnosis index. In order to solve this problem, an art designed to observe the coelom was disclosed in Japanese Patent Laid-Open No. 69839/1982 in which a pair of image guides is inserted into an insertion portion of an endoscope, the image guide having an objective lens at one end thereof and an ocular at the other end thereof, and the convergence angle formed by the pair of the objective lens and the subject point to be observed is made to be such that the subject point can be observed stereoscopically. However, in this art, the outer diameter of the insertion portion of the endoscope is made too large, causing patients to suffer some discomfort. The outer diameter of the endoscope is preferably as small as possible in order to reduce the sensation of discomfort experienced by a patient and to allow the observer to observe the isthmus of the coelom.

When any unevenness on the surface of a subject (organism) is to be measured, a scale is used, as disclosed in Japanese Patent Publication No. 20488/1986, in such a manner that the scale is applied to the subject. Another method is disclosed in Japanese Patent Laid-Open No. 110208/1980 in which laser beams are used.

According to the prior art disclosed in Japanese Patent Publication No. 20488/1986, since it is necessary for the subject and the scale to be brought into contact with each other, there is potential for the organism to be injured, and the endoscope is difficult to handle. Furthermore, since the allowable range that can be measured is a single point, it has been difficult to conduct wide range measurements.

On the other hand, according to the prior art disclosed in Japanese Patent Laid-Open No. 110208/1980, it is necessary for a special apparatus such as a laser beam to be instituted; otherwise measurement can only be conducted in units equivalent to the distance between light spots, and sufficient resolution cannot therefore be obtained. Furthermore, a problem arises in that normal observation is interfered with by the laser beams.

OBJECT AND SUMMARY OF THE INVENTION

It is an object of the present invention to provide a stereo endoscope apparatus which is able to perform a stereoscopic observation without involving any necessity of enlarging the outer diameter thereof.

It is another object of the present invention to provide a stereo endoscope apparatus which is suitable for use to diagonose the diseased parts.

In the present invention, at least a pair of optical guides is inserted into the insertion portion of the apparatus, the optical guide being capable of conducting an illuminating light and the light reflected from the portion to be observed, whereby while either of the optical conducts the illuminating light, the other optical guide conducts the light from the subject observed, and the subject can be observed in a stereoscopic manner by switching the optical guides between one state of use and.

BRIEF DESCRIPTION OF THE DRAWINGS

FIGS. 1 and 2 illustrate a first embodiment of the present invention, wherein

FIG. 1 is a view illustrating the structure of a stereo endoscope apparatus;

FIG. 2 is a timing chart illustrating the operation of the stereo endoscope apparatus;

FIGS. 3 and 4 illustrate a second embodiment of the present invention, wherein

FIG. 3 is a view illustrating the structure of the stereo endoscope apparatus;

FIG. 4 is a view illustrating optical guide changing means;

FIGS. 5 and 6 illustrate a third embodiment of the present invention, wherein

FIG. 5 is a view illustrating the structure of the stereo endoscope apparatus;

FIG. 6 is a timing chart illustrating the operation of the stereo endoscope apparatus;

FIGS. 18 to 21 illustrate a twelfth embodiment of the present invention, wherein FIG. 18 is a front elevational view of the front end portion of an insertion portion of an endoscope;

FIG. 19 is a disposition drawing illustrating the portion in the vicinity of the ocular unit;

FIG. 20 is a cross-sectional view taken along the line A—A' of FIG. 19;

FIG. 21 is a disposition drawing stereoscopically illustrating the portion in the vicinity of the ocular unit;

DETAILED DESCRIPTION OF PREFERRED EMBODIMENT

Figure 1:
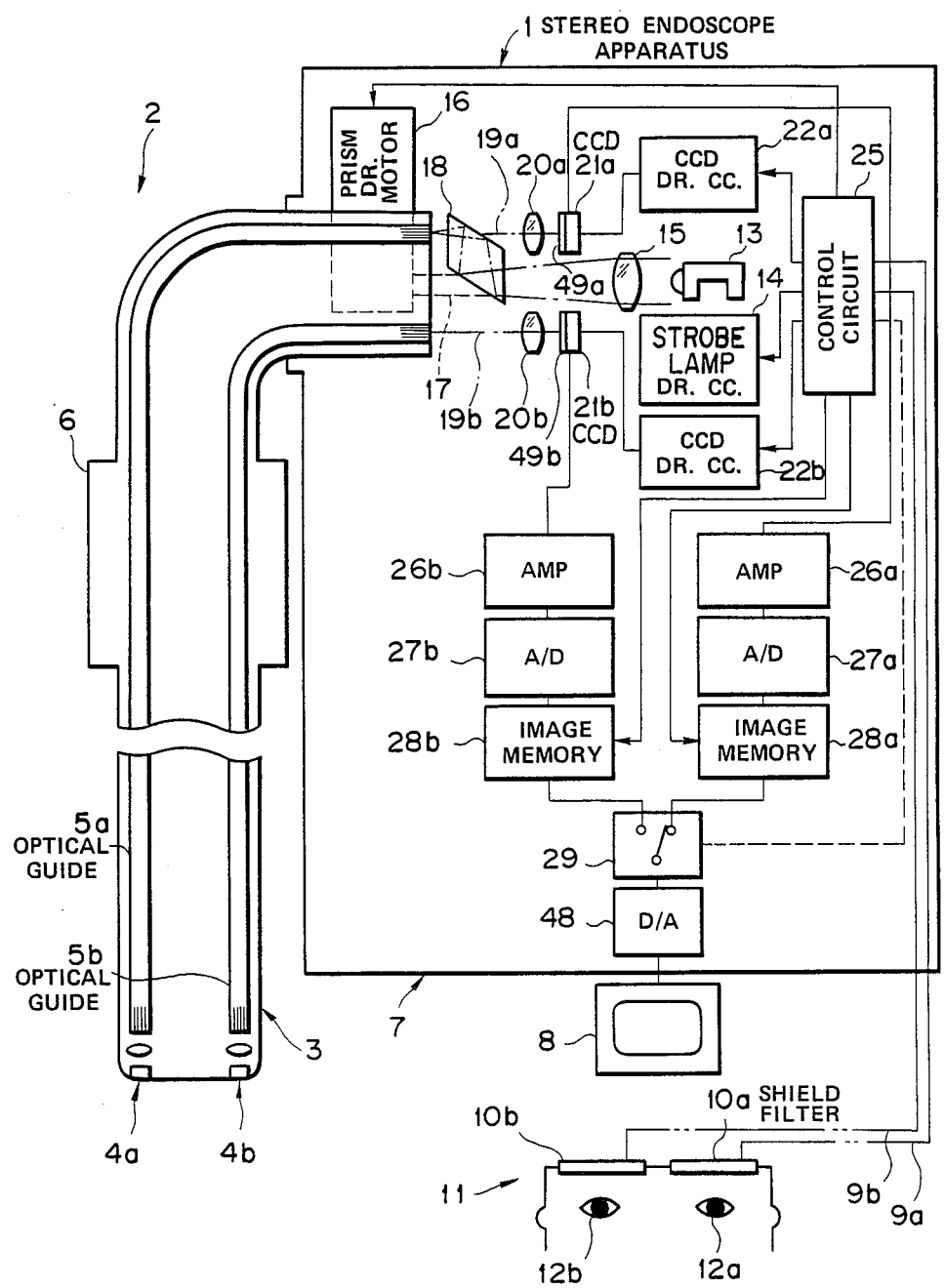

As shown in FIG. 1, a stereo endoscope apparatus 1 according to a first embodiment comprises: an endoscope 2 having an elongated insertion portion; a control unit 7 to which the endoscope 2 is able to be fitted, and which includes a light source portion, signal processing means, and control means; and a monitor 8 comprising a color CRT for displaying image signals output from the control unit 7.

At the front end of the elongated and flexible insertion portion 3 of the endoscope 2, objective lens systems 4a and 4b are disposed which are constituted by a pair of objective cover glasses confronting a position to be observed and an objective lens. This pair of objective lens systems 4a and 4b are positioned away from each other at a certain distance in order to obtain the parallax which realizes a stereoscopic view. Optical guides 5a and 5b projecting from the positions behind the objective lens systems 4a and 4b are inserted into an insertion portion 3, and designed to be able to be connected to the control unit 7 via an operation portion 6 of a large diameter connected to the rear end of the insertion portion 3.

An image displayed by the color CRT monitor 8 can be imaged on the right eye 12a or left eye 12b through, for example, shield glasses 11 having shield filters 10a and 10b, the shield glasses 11 being provided outside the control unit 7 with connecting cables 9a and 9b.

The shield filters 10a and 10b provided for the shield glasses 11 used by an operator comprises, for example, liquid crystal shutter which utilizes twistnematic liquid crystal. The twistnematic liquid crystal is constituted in such a manner that the liquid crystal is sandwiched by two deflector plates which are rotated by 90° to each other wherein when the electrode in the liquid crystal element is subjected to a voltage, any light is prevented from transmission, while when it is subjected to no voltage, light can transmit.

The structure of the control unit 7 will be described in detail.

The light source portion is constituted by: a strobe light 13 for emitting a illuminating light; a strobe lamp electricity supplying circuit 14 the output electricity of which is controlled by a control circuit 25 comprising a microprocessor or the like as the control portion thereof, and which supplies electricity to the strobe lamp 13; and a convergence lens 15 for converging the illuminating light emitting from the strobe lamp 13.

The illuminating light emitting from the strobe lamp 13 and transmitted through the convergence lens 15 is polarized by a prism 18 secured to a rotational shaft 17 of a prism driving motor 16 the rotation of which is controlled by the control circuit 25. The thus-polarized light is arranged to be made incident upon either end surface of a pair of the optical guides 5a or 5b made of fiber bundles.

An optical axis 19a extending perpendicular to the end surface of the optical guide 5a to the inside portion of the control unit 7 is provided with a solid state imaging element 21a with a light receiving lens 20a. On the other hand, an optical axis 19b extending perpendicular to the end surface of the optical guide 5b is provided with a solid state imaging element 21b with a light receipt lens 20b. A pair of color mosaic type of optical filters 49a and 49b are secured to the front surface of the solid state imaging elements 21a and 21b.

The solid state imaging element 21a is arranged to be connected to and thereby driven by a CCD driving circuit 22a which is controlled by the control circuit 25. Similarly, the solid state imaging element 21b is arranged to and driven by a CCD driving circuit 22b which is controlled by the control circuit 25.

The solid state imaging element 21a is connected to an amplifier 26a which amplifies the output signals from the solid state imaging element 21a, and is connected to an A/D converter 27a via this amplifier 26a, the A/D converter 27a conducting A/D conversion. This A/D converter 27a is arranged to be connected to an image memory 28a which is controlled by the control circuit 25.

Similarly, the solid state imaging element 21b is connected to an amplifier 26b, and is connected to an A/D converter 27b via this amplifier 26b. This A/D converter 27b is arranged to be connected to an image memory 28b which is controlled by the control circuit 25.

The image memories 28a and 28b are connected to a video switch 29 which is controlled by the control circuit 25, and is connected to the color CRT monitor 8 via the video switch 29 and a D/A converter 48.

The control circuit 25 controls the strobo lamp driving circuit 14 so as to light the strobe lamp 13, for example, 60 times per second, and controls, in synchronization with this lighting, the rotation of the prism driving motor 16 so as to make the prism 18 interpose 30 times between the optical axes 19a and 19b, respectively, and switches each image stored in the image memories 28a and 28b in synchronization with the video switch 29 so that the image is displayed by the color CRT monitor 8.

The control circuit 25 controls the shield filters 10a and 10b provided for the shield glasses 11 in such a manner that the shield filters 10a and 10b are made to be in the transmissible state or non-transmissible state in synchronization with the image displayed on the color CRT monitor 8.

The operation of the apparatus according to the first embodiment the structure of which has been described above will now be described.

Assuming that, the prism 18 which can be rotated by the prism driving motor 16 disposed in the control unit 7 is interposed between the optical axis 19a as shown in FIG. 1, the illuminating light emitted from the strobo lamp 13 due to the supply of the electricity from the strobo lamp driving circuit 14 is converged by the convergence lens 15. The thus-converged light is made incident upon the prism 18. This prism 18 polarizes the illuminating light and introduces the same to the end surface of the optical guide 5a formed by a fiber bundle. This optical guide 5a introduces, serving as a light guide, the illuminating light to the emerging end thereof at the front end of the insertion portion 3. The illuminating light emitted from this emerging end of the optical guide 5a illuminates the portion to be observed through the objective lens system 4a (the thus-illuminated portion to be observed is called a B-field). The light reflected from the B-field to be observed is made incident upon the end surface of the other optical guide 5b at the front end of the insertion portion 3. The optical guide 5b, serving as an image guide, introduces the light reflected from B-field to be observed into the rear end surface of the optical guide 5b at the fitting portion of the endoscope 2 fitted to the control unit 7. The light reflected from B-field is received by an image area through the light receiving lens 20b and the color mosaic type of optical filter 49b located at the front surface of the solid state imaging element 21b. At this time, a driving signal is supplied from the CCD driving circuit 22b to the solid state imaging element 21b, and an image signal of B-field is output, in response to the driving signal, by the solid state imaging element 21b. The image signal from B-field is amplified by the amplifier 26b, converted by the A/D converter 27b into a digital signal, and supplied to the image memory 28b wherein the signal is stored in the form of an image signal of B-field. The image signal of B-field stored in the image memory 28b is displayed in the form of the image of B-field by the color CRT monitor 8 due to switching conducted by the control circuit 25 so as to electrically connect the image memory 28b with the color CRT monitor 8. At this time, a voltage is applied by the control circuit 25 to the shield filter 10a provided for the shield glasses 11 through the connection cable 9a whereby the shield filter 10a is brought to a state in which light transmission is prevented. As a result of this, the image of B-field displayed by the color CRT monitor 8 passes through the shield filter 10b disposed to the shield glasses 11, and imaged on the left eye 12b.

In a state where the prism 18 has been rotated by the prism driving motor 16 and interposed between the optical axis 19b, the optical guide 5b introduces, serving as a light guide, the illuminating light, while the other optical guide 5a introduces, serving as an image guide, the light reflected from A-field. The light reflected from A-field is output in the form of an image signal from the solid state imaging element 21a in response to the driving signal from the CCD driving circuit 22a, and supplied to the image memory 28a via the amplifier 26a and the A/D converter 27a, wherein it is stored as an image signal of A-field. The image signal of A-field stored in the image memory 28a is displayed in the form of the image of A-field by the color CRT monitor 8 due to the switching conducted by the control circuit 25 electrically connecting the image memory 28a with the color CRT monitor 8. Furthermore, a voltage is applied by the control circuit 25 to the shield filter 10b provided for the shield glasses 11 through the connection cable 9b whereby the shield filter 10b is brought to a state in which light transmission is prevented. As a result of this, the image of A-field displayed by the color CRT monitor 8 passes through the shield filter 10a disposed to the shield glasses 11, and imaged on the right eye 12a.

As described above, the control circuit 25 performs such control that the image of A-field is observed with the right eye 12a, while the image of B-field is observed with the left eye 12b.

In FIG. 2, a state is shown in which the image of A-field and that of B-field are successively output to the color CRT monitor 8.

As illustrated, the image of A-field which is the portion to be observed is imaged on the right eye 12a since the shield filter 10b of the left eye 12b is brought to a light-stopped state, while the shield filter 10a of the right eye 12a is brought to a light-tranmissible state. The image of B-field is imaged on the left eye 12b since the shield filter 10a of the right eye 12a is brought to a light-stopped state, while the shield filter 10b of the left eye 12b is brought to a light transmissible state. By alternately switching, for example, 30 times per second, the shield filters 10a and 10b between the state in which the light transmission is prevented and the state in which light is allowed to pass through, the portion to be observed can be observed as a stereo image having the parallax between A-field and B-field due to the afterimage phenomenon.

As described above, according to the present invention, the stereo image can be obtained in which slight unevenness of the surface of the portion to be observed can be recognized. Furthermore, since a pair of optical guides 5a and 5b are alternately used as the light guide and the image guide, there is not any necessity for enlarging the outer diameter of the insertion portion 3 of the endoscope 2.

Although in this embodiment, the color mosaic type of electronic endoscope apparatus (it is also called a coincidence type) is used, a structure in which ocular lenses are provided as an alternative to the solid state imaging elements 21a and 21b may be employed, causing a macrographical observation to be realized.

Figure 3:
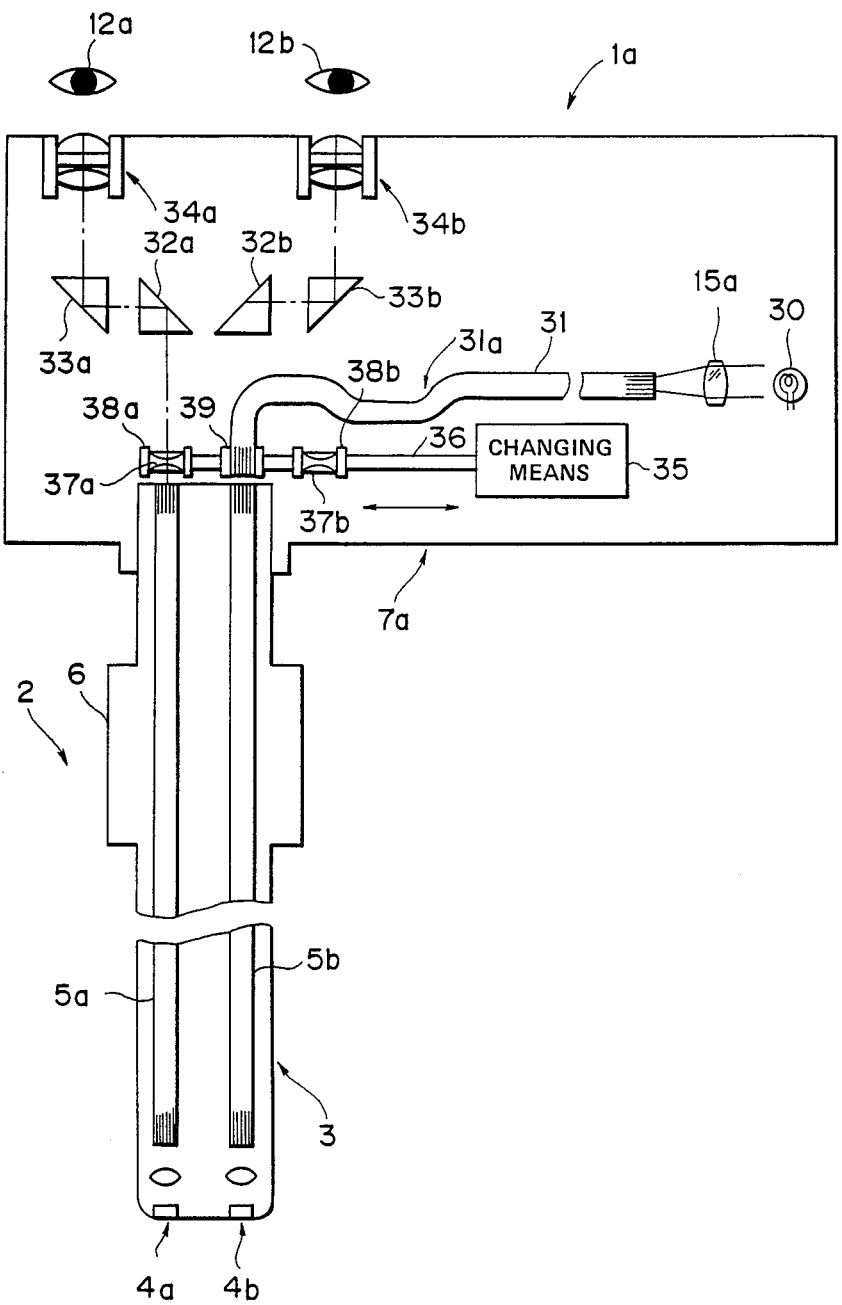
Figure 4:
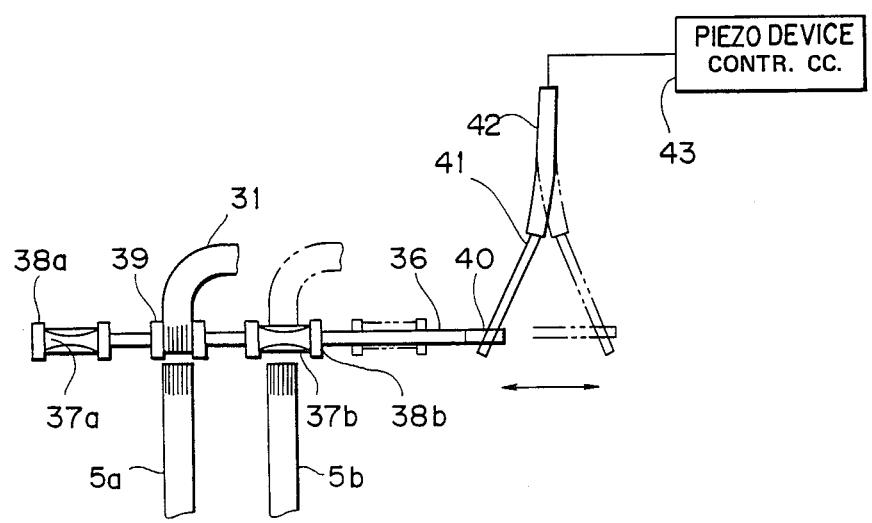

FIGS. 3 and 4 illustrate a second embodiment of the present invention, wherein FIG. 3 is a view illustrating the structure of a stereo endoscope apparatus and FIG. 4 illustrates means for switching optical guides.

The characteristic of this embodiment lies in that the present invention is subjected to an endoscope (called a "fiber scope" hereinafter) in which macrographical observation can be realized.

In FIG. 3, a stereo endoscope apparatus 1a comprises: the endoscope 2 the structure of which is the same as that described in the first embodiment; and a control unit 7a including the light source portion, observation optical system, and the means for switching the optical guides 5a and 5b.

The light source portion of the control unit 7a comprises: a light source lamp 30 for emitting illuminating light; a convergence lens 15a for converging the illuminating light emitted from the light source lamp 30; and a light guide 31 for introducing the illuminating light. The observation optical system of the control unit 7a comprises: prisms 32a and 33a for polarizing the light reflected from A-field which is the portion to be observed, the light being emitted from the end surface of the portion of the optical guide 5a at the portion for fitting with the control unit 7a; and prisms 32b and 33b for polarizing the light reflected from B-field which is the portion to be observed, the light being emitted from the end surface of the portion of the optical guide 5b at the similar portion. The system is constituted in such a manner that each light reflected from the portions to be observed, namely, A-field and B-field, is made incident upon the ocular systems 34a and 34b, respectively after they have been polarized by the prisms 32a and 33a and prisms 32b and 33b. As a result, the light is imaged on the right eye 12a or the left eye 12b. Canging means 35 for switching the optical guides 5a and 5b of the control unit 7a is constituted, for example, as shown in FIG. 4.

Referring to FIG. 4, a movable frame 36 is constituted in such a manner that the distances between a frame 38a thereof and a frame 39 thereof and between a frame 39 thereof and a frame 38b thereof are respectively the same as the distance between the optical guides 5a and 5b. It is arranged in such a manner that a relay lens 37a is arranged to be fitted within the frame 38a, a light guide 31 is arranged to be fitted within the frame 39, and a relay lens 37b is arranged to be fitted within the frame 38b. This movable frame 36 can be moved perpendicular to an optical axis connecting the end surfaces of the optical guides 5a and 5b with the prisms 32a and 32b. One end of the movable frame 36 is formed with an expanded portion 40 from which a driving rod 41 is projected. A piezoelectric element 42 such as a bimorph is continued from the driving rod 41. The piezoelectric element 42 is connected to a piezoelectric control circuit 43 where it is controlled. As a result of the movement of the movable frame 36, the relay lens 37a and the light guide 31 secured to the movable frame 36 are selectively and respectively disposed on the optical axes of the light guides 5a and 5b, and the light guide 31 and the relay lens 37ba are selectively and respectively disposed on the optical axes of the optical guides 5a and 5b.

The light guide 31 is arranged not to interfere with the movement of the movable frame 36 due to its curved portion 31a which can contract or expand at the time of this movement.

The operation of the thus-constituted apparatus according to the second embodiment will now be described.

Assuming that the movable frame 36 which is moved by the switching means disposed in the control unit 7a is in the state shown in FIG. 3, the illuminating light emitted from the light source lamp 30 is converged by the convergence lens 15a, made incident upon the end surface of the light guide 31 which end surface confronts the light source lamp 30, introduced by the light guide 31, and emerged from the opposite end surface. The thus-emitted illuminating light is transmitted through the optical guide 5b in a manner similar to the first embodiment in which the optical guide 5b serves as a light guide. The thus-transmitted light is issued to A-field which is the portion to be observed. The light reflected from A-field which is the portion to be observed is transmitted through the optical guide 5a which serves as an image guide through the objective lens system 4a, and issued from the end surface of the optical guide 5a which end surface confronts the relay lens 37a. The light reflected from A-field which is the portion to be observed is made incident upon the prisms 32a and 33a through the relay lens 37a, polarized by these prisms 32a and 33a, made incident upon the ocular system 34a, and imaged on the right eye 12a.

When the movable frame 36 is moved by the switching means 35 causing the light guide 31 and relay 37b to be disposed on the optical axes of the optical guides 5a and 5b, the illuminating light is introduced through the optical guide 5a which serves as a light guide, and the light reflected from B-field which is the portion to be observed is introduced through the optical guide 5b which serves as an image guide. As a result of this, the light reflected from B-field which is the portion to be observed is imaged on the left eye 12b.

That is, by alternately switching the light reflected from the portion to be observed having the parallax between A-field and B-field by way of switching the piezoelectric element 42 at 30 cycles, and imaging them to the right eye 12a and the left eye 12b, respectively, a stereo image can be observed due to an afterimage phenomenon.

As described above, the similar effect to the first embodiment can be obtained in this embodiment.

Furthermore, the stereo image may be observed by a TV monitor similarly to the first embodiment by connecting a TV camera to the ocular systems 34a and 34b.

Furthermore, the switching means may be constituted in such a manner that either of the relay lenses 37a or 37b and the light guide 31 are disposed on a rotatable disc and the-thus constituted disc is disposed at the central position between the optical guides 5a and 5b.

Figure 5:
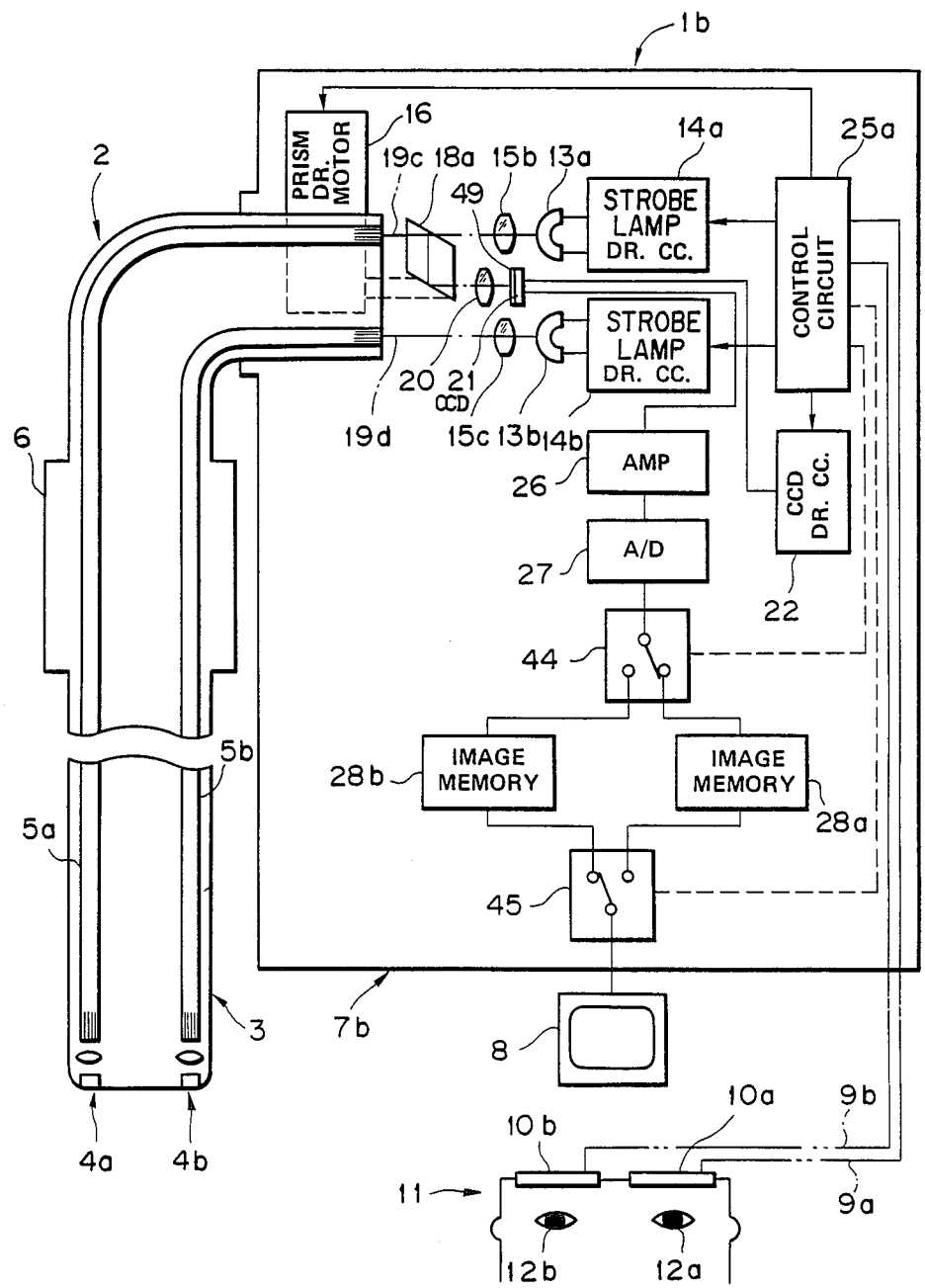
Figure 6:
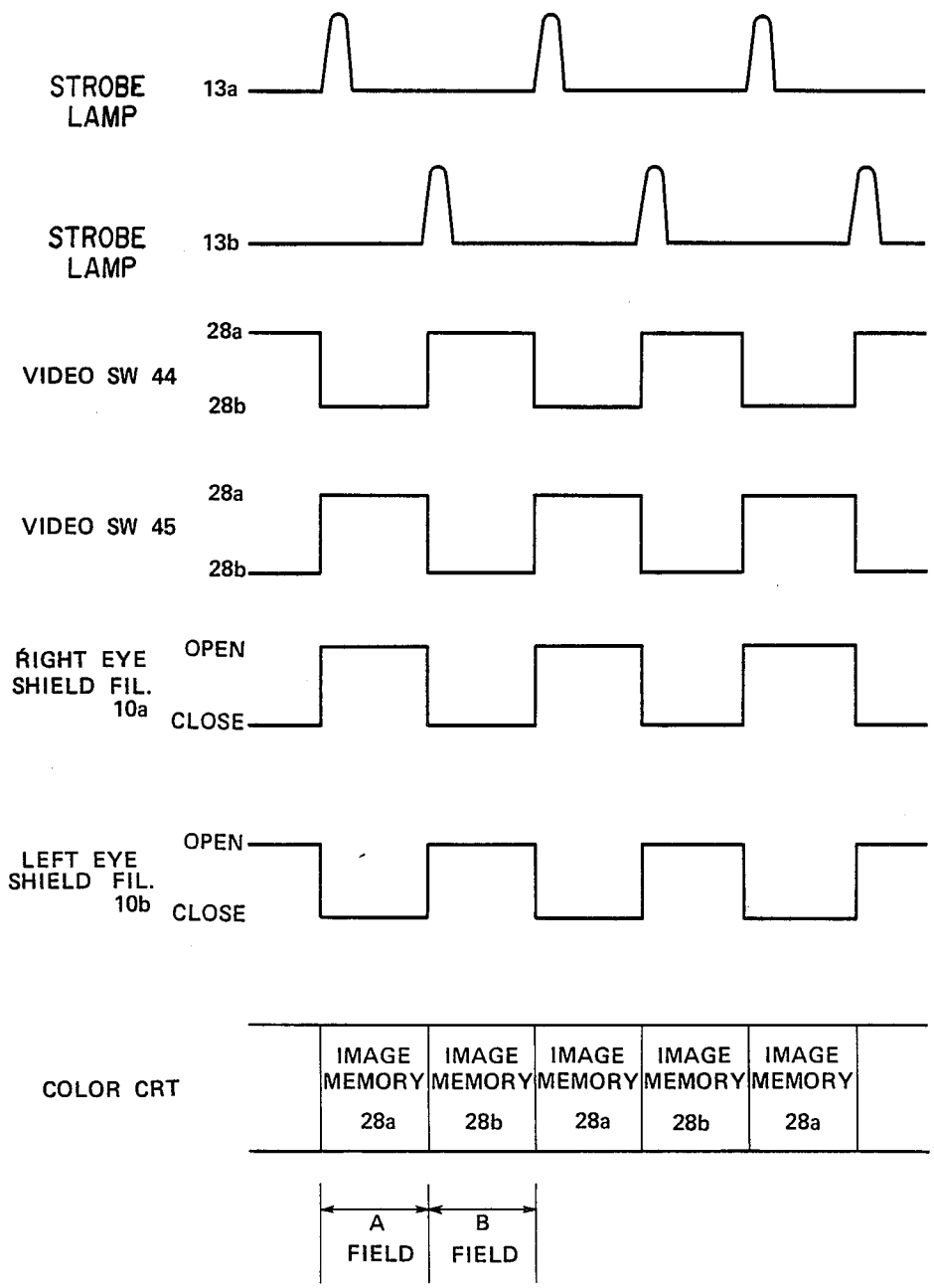

FIGS. 5 and 6 illustrate a third embodiment of the present invention wherein FIG. 5 illustrates the structure of a stereo endoscope apparatus, and FIG. 6 is a timing chart illustrating the operation of the stereo endoscope apparatus.

The characteristic of this embodiment lies in that the present invention is subjected to the electronic endoscope apparatus.

As shown in FIG. 5, the stereo endoscope apparatus 1b according to the third embodiment comprises: an endoscope 2 which can be inserted into the coelom and so forth; a control unit 7b connected to the endoscope 2 and accommodates a signal processing system and so forth; and a color CRT monitor 8 for displaying the image signal output from the control unit 7b.

The endoscope 2 and shield glasses 11 having the shield filters 10a and 10b and connected to the control unit 7b with the connecting cables 9a and 9b are constituted similarly to the first embodiment.

The structure of the control unit 7b will now be described.

Strobo lamps 13a and 13b are disposed, as light sources, on the optical axes 19c and 19d connecting the strobe lamps 13a and 13b with the end surfaces of the optical guides 5a and 5b. The outputs from the strobe lamps 13a and 13b are controlled by a control circuit 25a, and strobo lamp electricity supplying circuits 14a and 14b are connected to the strobe lamps 13a and 13b. The illuminating light beams emitted from the strobe lamps 13a and 13b are arranged to be converged by convergence lenses 15b and 15c on the optical axes.

Either of the illuminating light beams is arranged to be made incident upon the end surface of either of the optical guides 5a or 5b which is in the form of a fiber bundle.

A prism 18a extending from the prism driving motor 16 the rotation of which is controlled by the control circuit 25a polarizes the light reflected from the portion to be observed which light is emitted from the end surface of either of the optical guide 5a or 5b. The thus-polarized light is arranged to be received by a solid state imaging element 21 secured to the front surface of a color mosaic type of optical filter 49 through a light receiving lens 20. This solid state imaging element 21 is driven by a CCD driving circuit 22 which is controlled by the control circuit 25a, and outputs an electric signal corresponding to the light reflected from the portion to be observed. The electric signal is amplified by an amplifier 26, and converted by an A/D converter 27 into a digital signal. The digital signal corresponding to the light reflected from the portion to be observed is arranged to be selectively stored by either of the image memory 28a or 28b by a video switch 44 which is controlled by the control circuit 25a. The stored information on the light reflected form the portion to be observed is also controlled by the control circuit 25a, and displayed by the color CRT monitor 8 via a video switch 45 which conducts the selection opposite to that conducted by the video switch 44.

The operation of the thus-constituted apparatus according to the third embodiment will now be described.

Assuming that the prism 18a disposed in the control unit 7b is as shown in FIG. 5, the illuminating light emitted from the strobe lamp 13b strikes A-field which is the portion to be observed through the optical guide 5b interposed in the endoscope 21, the optical guide 5b serving as a light guide. The light obtained from A-field which is the portion to be observed is made incident upon the prism 18a through the optical guide 5a which serves as an image guide. The light reflected from A-field which is the portion to be observed is polarized by the prism 18a and received by the solid state imaging element 21. The light reflected from A-field which has been received is converted by the solid state imaging element 21 driven by the CCD driving circuit 22 into an electric signal, processed by the amplifier 26 and the A/D converter 27, and stored by the image memory 28a selected by the video switch 44 which is controlled by the control circuit 25a. The image information on A-field stored in the image memory 28a is displayed by the color CRT monitor 8 when the video switch 45 controlled by the control circuit 25a selects the image memory 28a in synchronization with the interposition of the prism 18a between the optical axis 19d caused by the rotation of the prism driving motor 16 controlled by the control circuit 25a.

At this time, the image on A-field is imaged on the right eye when the shield filter 10a disposed to the shield glasses 11 controlled by the control circuit 25a is brought to a light-transmissible state, and the shield filter 10b disposed to the same is brought to a light-transmission prevented state.

Similarly, the image on B-field is imaged on the left eye.

By alternately lighting the strobe lamps 13a and 13b, for example, 30 times per second, by the control circuit 25a, rotating in synchronization of this, the prism 18a by the prism driving motor 16 so as to alternately using the optical guides 5a and 5b as a light guide or an image guide, and alternately making the video switches 44 and 45 synchronize alternately, the image on A-field is imaged on the right eye, while the image on B-field is imaged on the left eye as shown in FIG. 6.

As a result of this, the portion to be observed can be observed stereoscopically by virtue of the parallax between A-field and B-field and after image phenomenon.

Therefore, the effect similar to that obtained in the first embodiment can be obtained.

Figure 7:
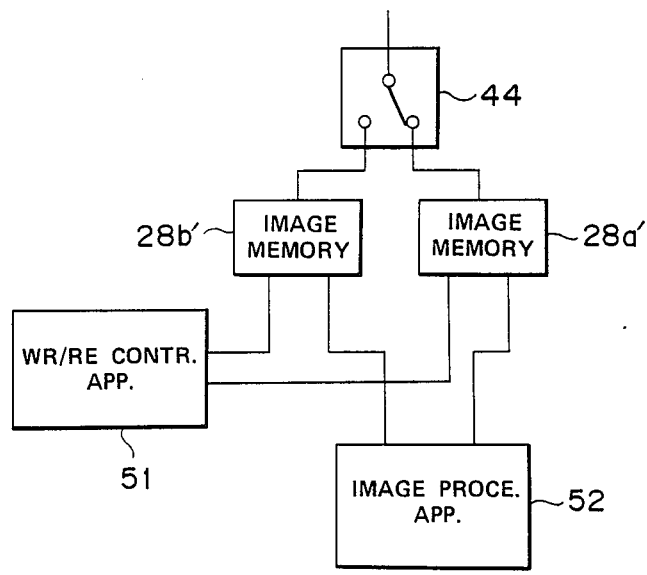
FIG. 7 is a block diagram illustrating an essential portion of a modification of the third embodiment.

FIG. 7 illustrates an essential portion in a modification of the third embodiment. The digital signal transmitted through the video switch 44 shown in FIG. 5 or FIG. 7 is selectively stored by either of image memory 28a' or 28b' shown in FIG. 7. The image memories 28a' and 28b' are controlled by a write/read control apparatus 51 in their writing and reading digital signals. For example, in a write mode, the digital signal which has been passed through the video switch 44 is written and stored, while in a reading mode, the stored digital signals are retained (they are not cleared) and read out.

The digital signals read from the image memories 28a' and 28b' are supplied to an image processing apparatus 52. The image processing apparatus 52 can employ a type of the apparatus such as that disclosed in Japanese Patent Application No. 168791/1987. However, since the relative positional information between the right and left images to be imaged which is required in the apparatus disclosed in Japanese patent application No. 168791/1987 is uniformly determined in this modification depending upon the dimensions and the shape of the front end portion of the scope, it can be previously supplied as a predetermined data to the image processing apparatus.

According to this modification, the right and left image signals are converted into a digital manner, and passes through the video switch 44 so that the digital signal corresponding to the left image is stored by either of the image memory 28a' or 28b', while the digital signal corresponding to the right image is stored by the other image memory. Then, it is retained by the image memories 28a' and 28b' respectively, and sent to the image processing apparatus 52.

From the image processing apparatus 52, the absolute information on distance such as the height and the size of the portion to be observed can be obtained similarly to that obtained in the apparatus disclosed in Japanese Patent Application No. 168791/1987.

As described above, in this modification, by realizing the connection with the image processing apparatus 52, the objective and useful information such as information on the distance of the portion to be observed can be obtained, whereby an advantage of capability of performing a correct diagonosis can be exhibited.

A variety of types can be utilized as the image processing apparatus 52 without limitation to the description.

Furthermore, this modification is not a modification which opposes the third embodiment (this modification is not a modification which cannot exist together the third embodiment). For example, by disposing the structure arranged from the output of the video switch 44 in parallel to the structure shown in FIG. 7 (omitted from the illustration) in addition to the structure shown in FIG. 5, an apparatus can be realized in which the stereo observation and stereo measurement by image process can be simultaneously conducted. A still further variation can be applied.

Figure 8:
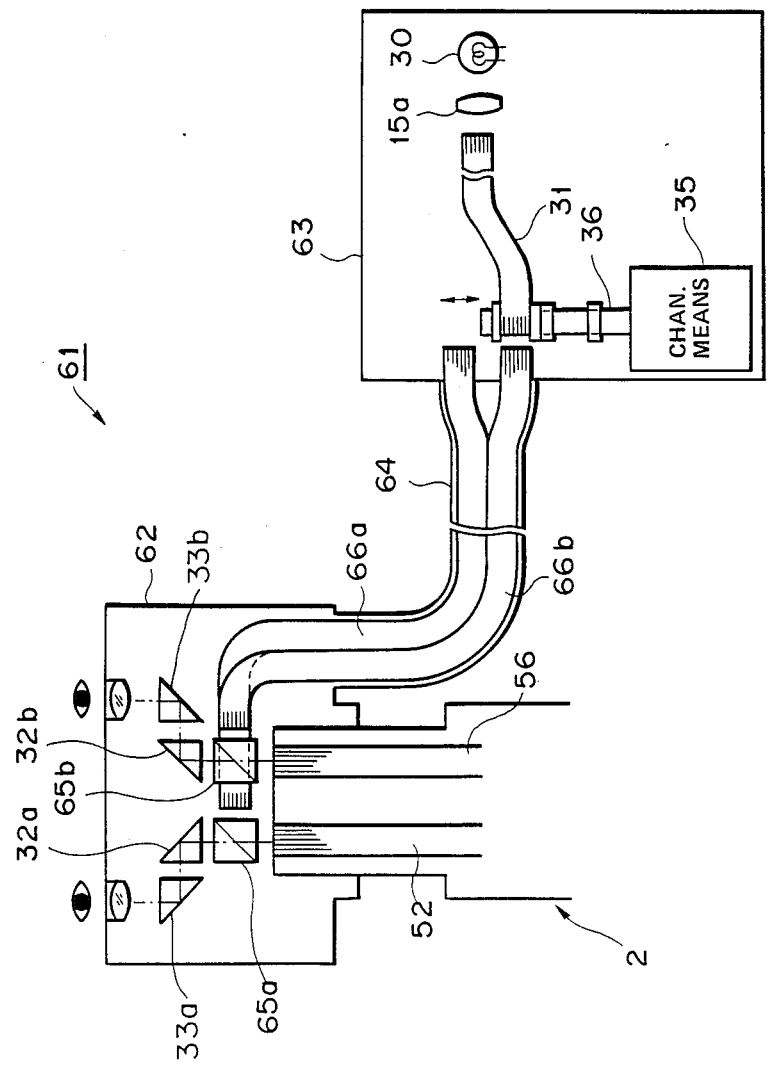
FIG. 8 is a disposition drawing illustrating an essential portion of a fourth embodiment.

FIG. 8 illustrates a stereo endoscope apparatus 61 according to a fourth embodiment.

This fourth embodiment is the development of the embodiment shown in FIG. 3, wherein the control unit 7a shown in FIG. 3 is divided into an ocular unit 62 and a light source unit 63, and these units 62 and 63 are connected by a light cable 64.

The ocular unit 62 comprises beam splitters 65a and 65b disposed confronting the end surface of the optical guides 5a and 5b in the endoscope 2 so that the light is branched into the reflecting and transmitting directions. Light guides 66a and 66b are disposed confronting one side of the branching directions of the beam splitters 65a and 65b, while prisms 32a and 32b shown in FIG. 3 are disposed confronting the other side of the same.

The light guides 66a and 66b are inserted into the light guide cable 64 extending from the ocular unit 62, and arranged to be fitted to a connector receiver of the light source apparatus 64. The other structure is the same as the apparatus according to the second embodiment.

The illuminating light from the lamp 30 can be alternately supplied to the incidental surfaces of the two light guides 66a and 66b similarly to the second embodiment. As shown in FIG. 8, when a light guide 31 confronts the light guide 66b, the illuminating light from the lamp 30 is supplied to the ocular unit 62 through the light guide 66b, reflected, for example by halves, by the beam splitter 65b, and supplied to the optical guide 5b. With the illuminating light supplied through the optical guide 5b, the subject can be illuminated. The illuminated subject is imaged by the objective lens 4a on the end surface of the optical guide 5a, and supplied to the end surface of the same adjacent to the ocular unit 62. The optical image supplied through the optical guide 5a can be observed via the beam splitter 65a, prisms 32a and 33a and the ocular lens 34a.

By activating the switching means 35, the light guide 31 can be made to oppose the light guide 65a. In this state, the light guide 5a transmits the illuminating light, while the optical guide 5b transmits the optical image. The optical image can be observed via the beam splitter 65b, prisms 32b and 33b and the ocular lens 34b.

According to the fourth embodiment, since the ocular unit 62 is individually provided from the light source means, the size of the apparatus can be reduced. Furthermore, since the ocular unit 62 does not have any moving means, the size of the unit can be reduced and it works well.

Figure 9:
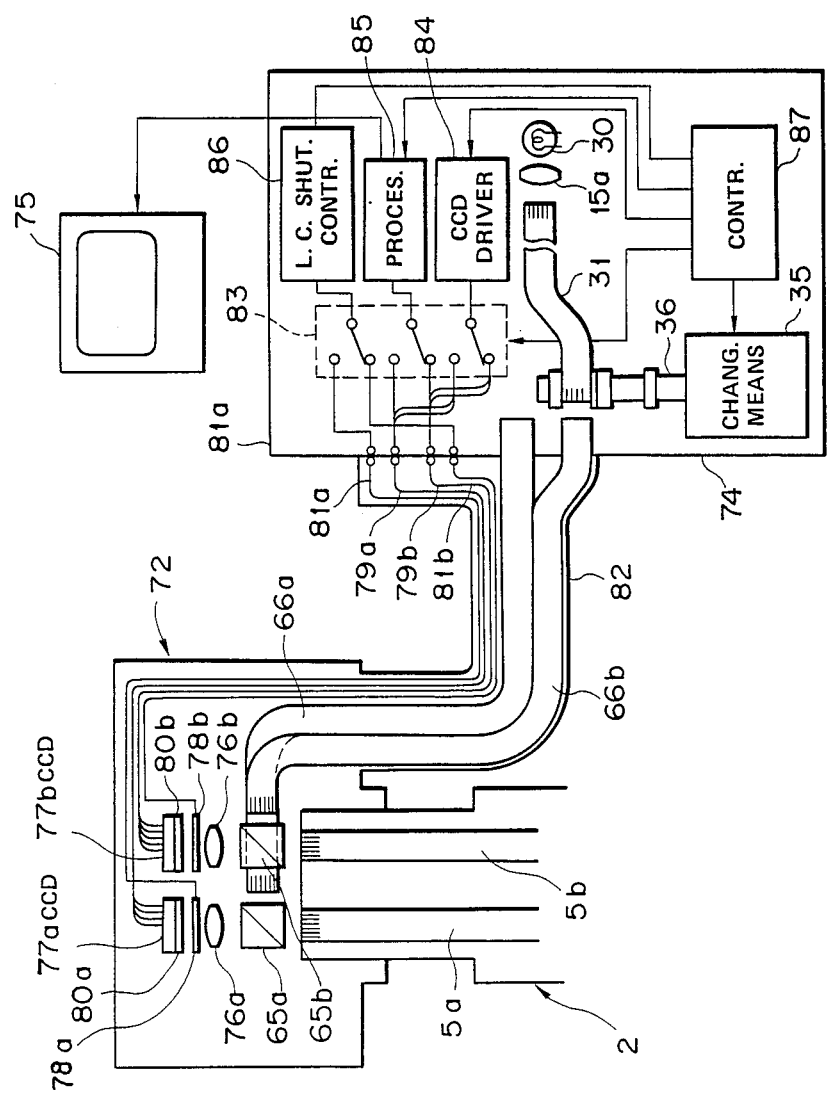
FIG. 9 is a disposition drawing illustrating an essential portion of a fifth embodiment.

FIG. 9 illustrates a stereo endoscope apparatus 71 according to a fifth embodiment of the present invention.

According to the fifth embodiment, a stereo image can be obtained with the use of an imaging unit 72 although the stereo image can be obtained by naked eye observation, in the fourth embodiment.

The stereo endoscope apparatus 71 comprises: the endoscope 2; an imaging unit 72 fitted to the endoscope 2; a control unit 74 including light source means for supplying illuminating light to the imaging unit 72 and signal processing means; and a display monitor 75.

The imaging unit 72 comprises imaging lenses 76a and 76b provided as an alternative to the prisms 32a and 32b shown in FIG. 8. At the imaging points of the imaging lenses 76a and 76b, CCDs 77a and 77b are respectively disposed, whereby the optical image supplied through the optical guides 5a and 5b can be imaged on the imaging surfaces of the CCDs 77a and 77b. The CCDs 77a and 77b includes color mosaic filters 80a and 80b respectively at the front surfaces thereof, and liquid crystal shutters 78a and 78b are respectively disposed in front of the CCDs 77a and 77b. As a result of this, when the CCD 77a (or 77b) is in a state in which the image is exposed, the other CCD 77b (or 77a) is in a state in which light transmission is prevented.

The light guides 66a and 66b disposed confronting the beam splitters 65a and 65b, signal cables 79a and 79b connected to the CCDs 77a and 77b, and signal cables 81a and 81b connected to the liquid crystal shutters 78a and 78b are inserted into a universal cable 82 extending outwardly from the imaging unit 72. An end of the universal cable 82 is provided with a connector which can be coupled to the connector receiver of the control unit 74 so that the illuminating light can be supplied to the light guides 66a and 66b similarly to the fourth embodiment. The signal cables 79a, 79b, 81a, and 81b are connected, through a switch 83, to a CCD driver 84, a processing circuit 85 and a liquid crystal shutter control circuit 86.

The switch 83, CCD driver 84, processing circuit 85, liquid crystal shutter control circuit 86 and switching means 35 are controlled by a controller 87. For example, when the mode to supply the illuminating light to the light guide 66b as shown in FIG. 9 is instructed, the controller 87 controls the switching means 35 so as to make the switch 83 select contacts as shown in FIG. 9. In this state, the liquid crystal shutter 78b is retained in a state in which light transmission is prevented, and a reading drive signal is supplied from the CCD driver 84 to the CCD 77b. The signal which has been read out is supplied to the processing circuit 85 wherein the signal is processed. In this state, the other CCD 77a is retained in an exposure state. Then, they are switched other after, for example, a time period of 1/30 or 1/60 [sec] has been elapsed.

The image signal generated by way of signal-processing by the processing circuit 85, is displayed by the monitor 75. The processing circuit 85 includes two frame memories for storing the signals read by the two CCDs 77a and 77b so that the signals are alternately read out and displayed by the same monitor 75. The images alternately displayed by the monitor 75 are stereoscopically imaged with the use of, for example, the shield filters 10a and 10b as shown in the first embodiment.

Figure 10:
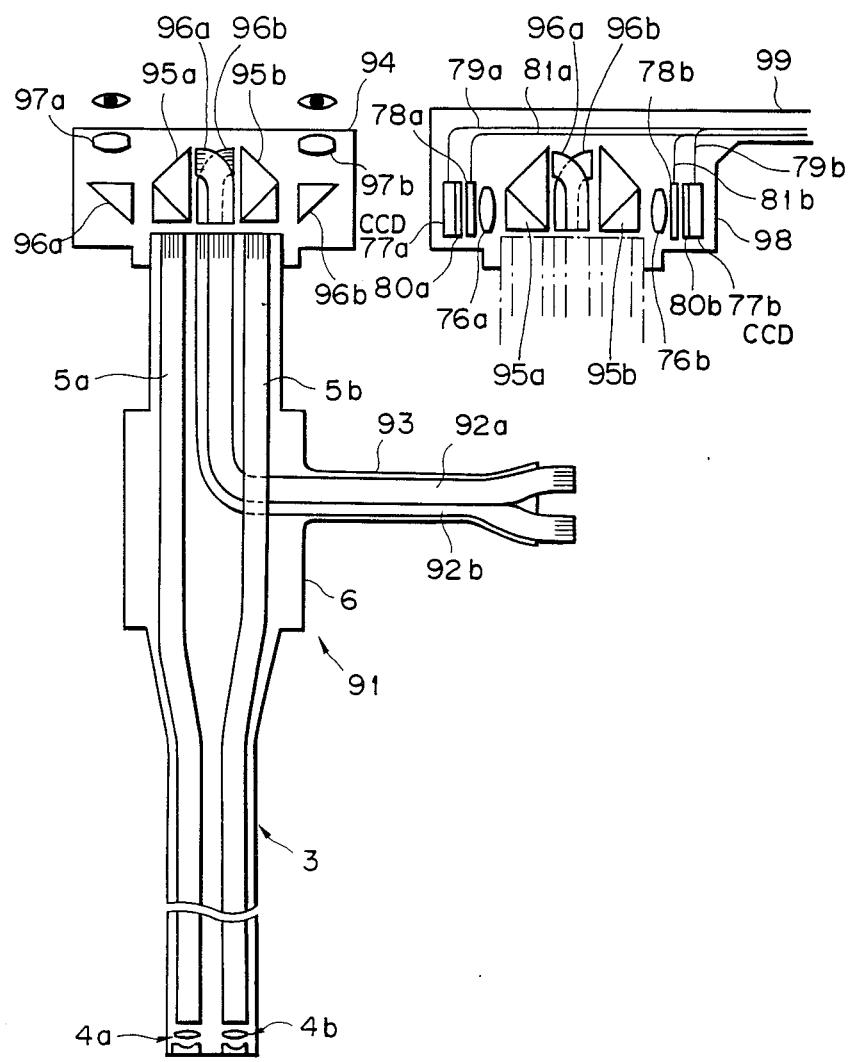
FIG. 10 is a disposition drawing illustrating an essential portion of a sixth embodiment.

FIG. 10 illustrates an essential portion of a sixth embodiment.

An endoscope 91 according to this embodiment is provided with two light guides 92a and 92b in comparison to the endoscope 2 shown in FIG. 1. The two light guides 92a and 92b are inserted into a light guide cable 93 extending from the operation portion 6 and the inside portion of the endoscope 91 behind (portion adjacent to the ocular portion) the operation portion 6. Since it is not inserted into the insertion portion 3, the outer diameter 3 does not become enlarged.

An ocular unit 94 which can be fitted to the endoscope 91 is provided with beam splitters 95a and 95b at the positions confronting the optical guides 5a and 5b. One pair of end surfaces of short light guides 96a and 96b are disposed confronting the light issuing end surfaces of the light guides 92a and 92b, while the other end surfaces of the same are made to confront the beam splitters 95a and 95b. Prisms 97a and 97b are disposed confronting the beam splitters 95a and 95b so that light is introduced into the ocular lenses 98a and 98b.

The end portion of the light guide cable 93 can be fitted to, for example, the light source unit 63 shown in FIG. 8.

When the illuminating light is transmitted through the light guide 92a in a state where the ocular unit 94 is fitted, the illuminating light is transmitted to the light guide 96a in the ocular unit 94, and again transmitted to the optical guide 5a in the endoscope 91 via the beam splitter 95a. On the other hand, the optical image transmitted by the optical guide 5b can be observed through the beam splitter 95b, prism 96b, and the ocular lens 97b. To the endoscope 91, an imaging unit 98 can be fitted as shown in FIG. 10b as an alternative to the ocular unit 94.

This imaging unit 98 includes imaging lenses 76a and 76b confronting the beam splitters 95a and 95b as an alternative to the prisms 96a and 96b in the ocular unit 94. By virtue of the imaging lenses 76a and 76b, image can be formed on the CCDs 77a and 77b. In front of the CCDs 77a and 77b, the color mosaic filters 80a and 80b are fitted, and the liquid crystal shutters 78a and 78b are fitted in front of the color mosaic filters 80a and 80b. The signal cables 79a, 79b, 81a, and 81b connected to the CCDs 77a and 77b and the liquid crystal shutters 78a and 78b are inserted into a signal cable 99.

According to the sixth embodiment, since it is not necessary for the light guide cable to be extended from the ocular unit 94, the light guide cable will not interfere with the observation, whereby the operability can be improved. Furthermore, a stereoscopic image can be obtained with the use of the ocular unit 94, and the image displayed on the monitor in the stereoscopic form can be observed with the use of the imaging unit 98.

Figure 11:
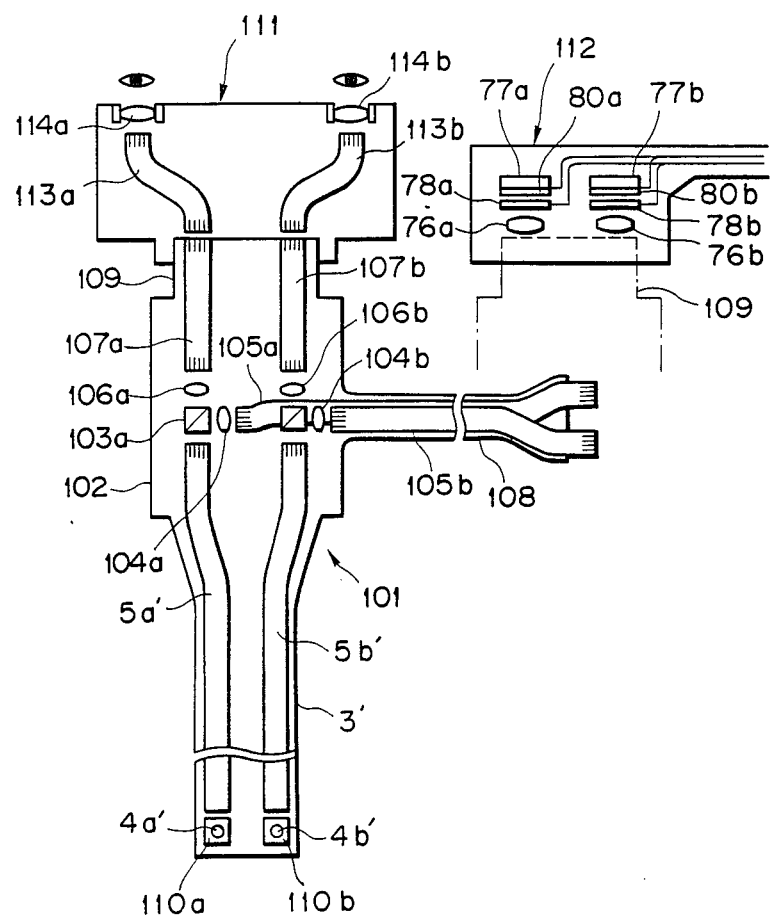
FIG. 11 is a disposition drawing illustrating an essential portion of a seventh embodiment.

FIG. 11 illustrates an essential portion according to a seventh embodiment of the present invention.

An endoscope 101 according to the seventh embodiment is provided with beam splitters 103a and 103b in an operation portion 102 thereof. The illuminating light transmitted through the light guides 105a and 105b disposed via lenses 104a and 104b which confront the beam splitters 103a and 103b can be transmitted to optical guides 5a' and 5b', while the optical image transmitted by the optical guides 5a' and 5b' can be transmitted to image guides 107a and 107b disposed via lenses 106a and 106b which confront the beam splitters 103a and 103b. In this embodiment, the endoscope 101, is, for example, a tilted type. That is, the side portion of an insertion portion 3' is provided with objective openings to which object lenses 4a' and 4b' are fitted. The light beams transmitted through the object lenses 4a' and 4b' are reflected from the triangular prisms 110a and 110b, and imaged at the end surfaces of the image guides 107a and 107b. The light guides 105a and 105b are inserted into a light guide cable 108 which extends from the operation portion 102.

The image guides 107a and 107b are projected to a fitting portion 109 behind the operation portion 102. An ocular unit 111 or an imaging unit 112 can be fitted to the fitting portion 109.

Image guides 113a and 113b which confront the image guides 107a and 107b are provided in the ocular unit 111 so that a stereo image can be obtained through the ocular lenses 114a and 114b.

As an alternative to the ocular unit 111, an imaging unit 112 can be fitted to the endoscope 101 for the purpose of obtaining a stereoscopic image.

According to this embodiment, since the light is branched in the operation portion 102, the structure of the ocular unit 111 and the imaging unit 112 can be simplified, made compact and thereby made light weight.

Figure 12:
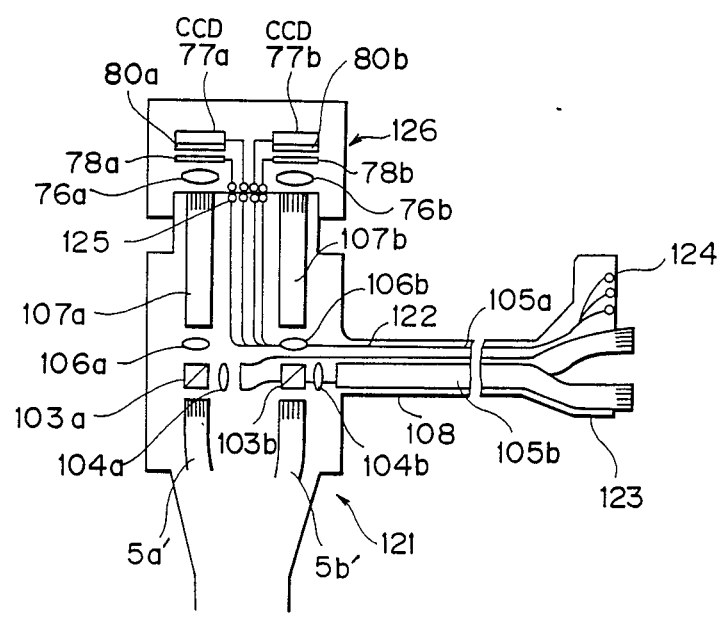
FIG. 12 is a disposition drawing illustrating an essential portion of a eigth embodiment.

A stereo endoscope apparatus 121 according to an eighth embodiment is shown in FIG. 12.

The stereo endoscope 121 is so constituted that a signal cable 122 is further inserted into the endoscope 101 shown in FIG. 11. This signal cable 122 is inserted into the cable 108 which extends outwardly from an operation portion 106, and connected to a contact 124 of a connector 123 fitted to the end portion of the cable 108. The other end of the signal cable 122 is connected to a contact 125 fitted to a fitting portion 109.

An imaging unit 126 which is able to be fitted to this endoscope 121 is constituted in such a manner that the signal cables 79a, 79b, 81a, and 81b of the CCD 77a and 77b and the liquid crystal shutters 78a and 78b of the imaging unit 112 shown in FIG. 11 are connected to a contact 127 provided at the portion which is mounted on the fitting portion of the endoscope 109.

The other structure is the same as that of the seventh embodiment.

According to the eighth embodiment, since it is not necessary for the imaging unit 126 to extends its signal cable outwardly, the operability can be improved.

Figure 13:
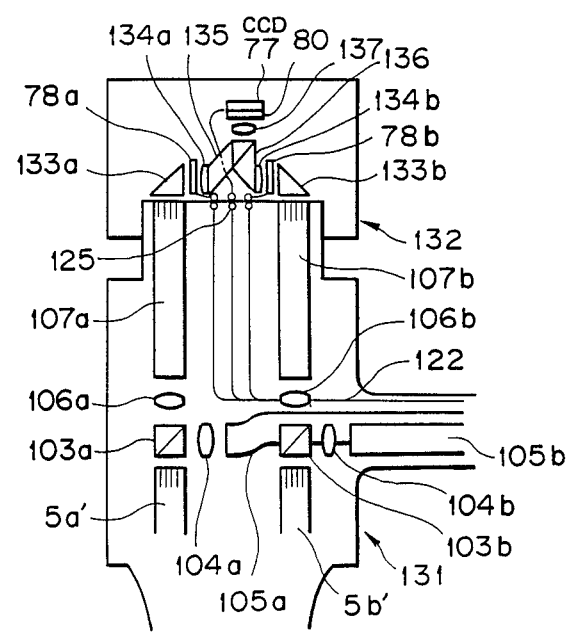
FIG. 13 is a disposition drawing illustrating an essential portion of a ninth embodiment.

FIG. 13 illustrates an essential portion of a ninth embodiment of the present invention.

An endoscope 131 according to this embodiment is so constituted that the number of the signal cables of the endoscope 121 shown in FIG. 12 is reduced (the number of the contacts 124 and 125 is of course reduced).

An imaging unit 132 is so constituted that the imaging unit 126 shown in FIG. 12 employs a common CCD 77 as an alternative to the two CCDs 77a and 77b.

In order to use the CCD 77, prisms 133a and 133b are disposed confronting the image guides 107a and 107b. The optical image transmitted through the image guide 107a via the prism 133a is imaged on the CCD 77 via the liquid crystal shutter 78a, lens 134a, prism 135 and beam splitter 136, and the lens 137. On the other hand, the optical image transmitted through the image guide 107b is imaged on the CCD 77 via the prism 133b, liquid crystal shutter 78b, lens 134b, beam splitter 136, and lens 137.

Figure 14:
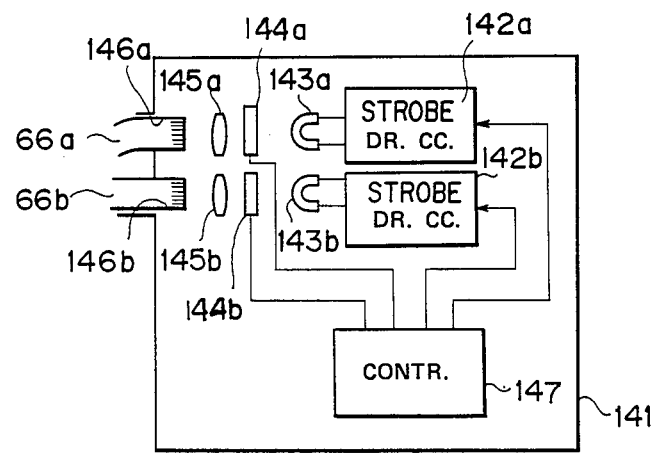
FIG. 14 is a disposition drawing illustrating a light source unit of a tenth embodiment.

FIG. 14 illustrates a light source unit 141 according to a tenth embodiment of the present invention.

This light source unit 141 includes two illuminating means.

That is, the illuminating light from strobe lamps 143a and 143b to which an electricity for illuminating them is supplied from the strobe driving circuits 142a and 142b is supplied to the light incident surface of the light guides 66a and 66b (for example, those shown in FIG. 8) via liquid crystal shutters 144a and 144b and lenses 145a and 145b, the light guides 66a and 66b being connected to the connector receivers 146a and 146b.

The strobe driving circuits 142a and 142b and the liquid crystal shutters 144a and 144b are controlled by a controller 147.

For example, when a trigger signal is supplied to the strobe driving circuit 142a so as to make this strobo emit light, the strobe driving circuit 142a supplies a pulse-shaped driving power to the strobe lamp 143a so as to make this strobe emit light. The illuminating light due to the strobe light is converged by a lens 145a via a liquid crystal shutter 144a, and made incident upon the end surface of the light guide 66a. In this state, the other strobe lamp 143b is not supplied with the electricity for strobe lighting and the liquid crystal shutter 144b is retained in a state in which light transmission is prevented. Then, after, for example, a time period of 1/30 or 1/60 [sec] has been elapsed, they are arranged to be switched with each other.

The light source unit 141 exhibits an advantage in that the illuminating light can be alternately supplied to the two light guides 66a and 66b without any necessity involved for providing any mechanical moving mechanism.

Figure 15:
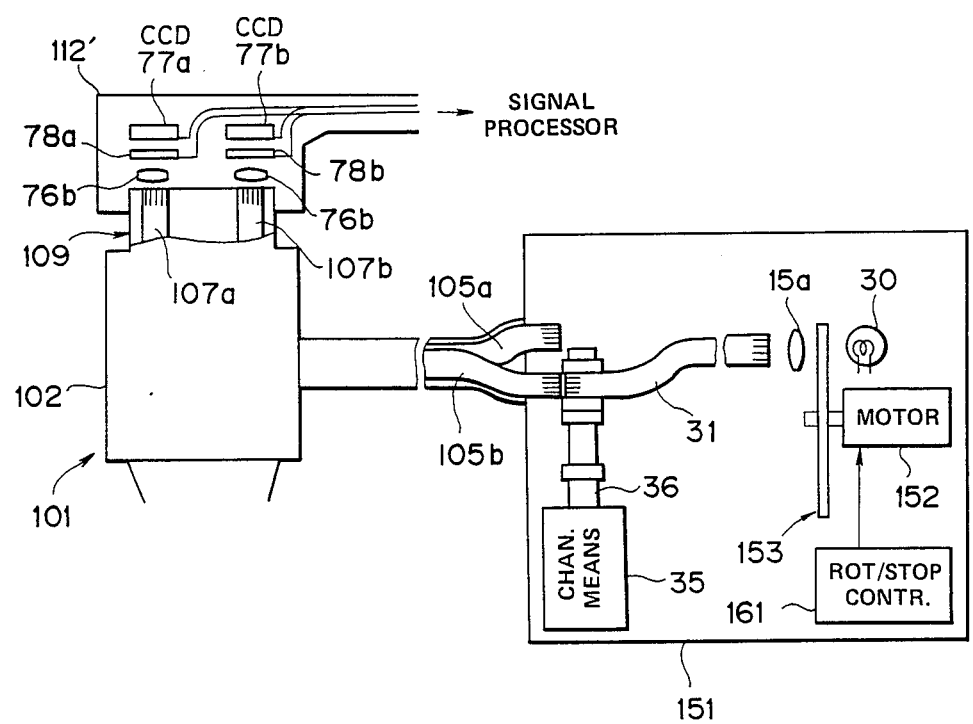
FIG. 15 is a disposition drawing illustrating a light source unit of a eleventh embodiment.

Although in the embodiments described above, a white light illumination and the imaging means having color mosaic filters are used, face successive type imaging means without using the color mosaic filter can be used. For example, in an imaging unit 112 shown in FIG. 11b, an imaging unit without the color mosaic filters 80a and 80b but having the CCDs 76a and 76b, that is, an imaging unit 112' shown in FIG. 15 may be used. In this case, the ends of the light guides 105a and 105b of the endoscope 101 are connected to a face successive type of light source unit 151 according to an eleventh embodiment which can output the white light.

This light source unit 151 is so constituted that a rotatable filter 153 rotated by a motor 152 is interposed between the lamp 30 and the lens 15a in the light source unit 63 shown in FIG. 8.

Figure 16:
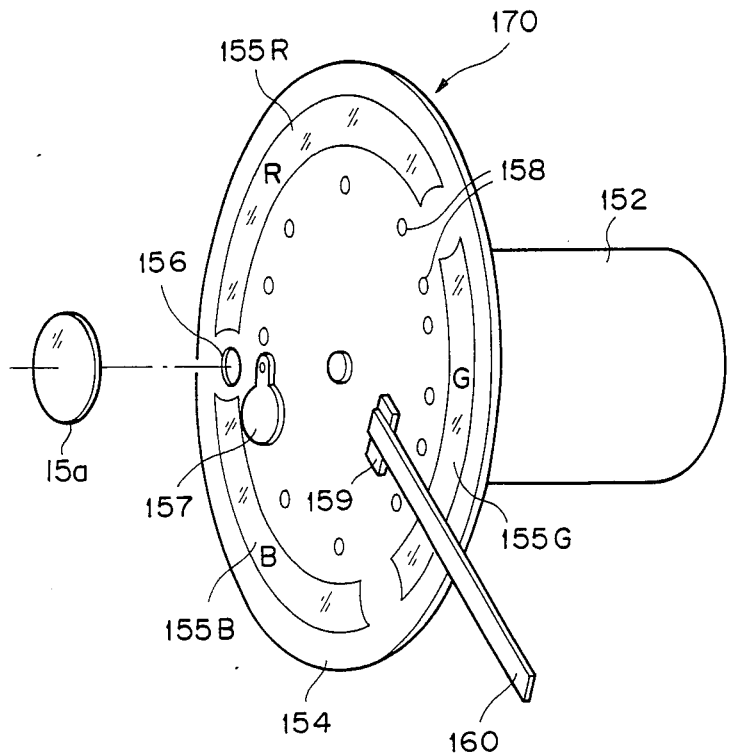
FIG. 16 is a perspective view of a rotatable filter according to the eleventh embodiment.

As shown in an enlarged view FIG. 16, the rotatable filter 153 is provided with red color-transmissible filter 155R, green color-transmissible filter 155G, and blue color transmissible filter 155B at a filter frame 154 thereof. Furthermore, an opening 156 for white illumination is disposed, for example, between the red color-transmissible filter 155R and the blue color-transmissible filter 155B, the portion between the red color-transmissible filter 155R and the blue color-transmissible filter 155B being the portion where light transmission is prevented. The opening 156 can be prevented from light transmission by a shield plate 157 which is provided rotatably relative to a point pivoting the shield plate 157 on a segment which connects between the center of the rotatable filter 153 and this opening 156.

Figure 17:
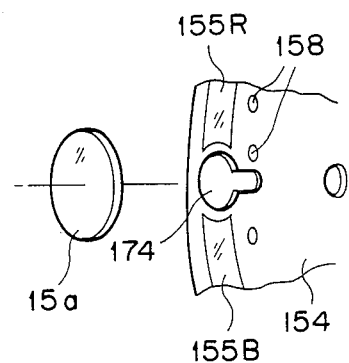
FIG. 17 is a perspective view illustrating parts of the rotatable filter according to the eleventh embodiment when it is being rotated.

That is, when the filter frame 154 is being rotated by the motor 152, the center of the annular portion in which light transmission is prevented and the point pivoting the shield plate 157 are, as shown in FIG. 17, aligned in the radial direction due to a centrifugal force. In this state, the opening 156 is covered by the shield plate 157, whereby the normal red, green, and blue face-successive illumination can be conducted.

On the other hand, when the rotation is stopped, since no centrifugal force is generated, the shield plate 157 is withdrawn from the opening 156.

The filter frame 154 is position-controlled in such a manner that the opening 156 thereof is disposed on an optical axis connecting the lamp 30 and a lens 15a. In order to perform this control or detect a timing for reading the CCDs 76a and 76b at the time of face-successive illumination, a multiplicity of apertures 158 is provided in the filter frame 154 in the circumferential direction, and light emitting elements and photosensors 159 are disposed to both sides of the filter frame 154, whereby a position-detecting rotary encoder is constituted. In FIG. 16, the photosensor 159 is fitted to the front end of the sensor mounting plate 160.

The motor 152 is controlled in its rotation/stop by a rotation/stop control circuit 161. For example, in a case where the face-successive type imaging unit 112' is used, the face-successive type color imaging can be performed by rotating the motor 152 so as to output the face-successive light.

On the other hand, in a case where the imaging unit 112 or the ocular unit 111 shown in FIG. 11b is used, the rotation of the motor 152 is stopped so as to realize a state in which the white light is output. As a result of this, the light source unit 151 can be used in a case of the face-successive type of color imaging, color imaging means including the mosaic filter, and the naked eye observation using the ocular unit 111. The rotation/stop of the motor 152 may be conducted by a manual switch.

In a case of the face-successive type, for example, in FIG. 1, the image memories 28a and 28b are constituted by three frames, and the signals imaged under the illumination of red, green and blue respectively are written in each frame memory. By simultaneously reading out the image data in the three frame memories, the digital color signals corresponding to red, green, and blue can be reproduced. These red, green and blue color signals are converted by the D/A converter into analog signals, whereby they can be displayed by a color monitor.

Next, a twelfth embodiment according to the present invention will now be described with reference to FIGS. 18 to 22.

This embodiment is characterized in that three image guides are used, and one of them can be used as a light guide.

Figure 18:
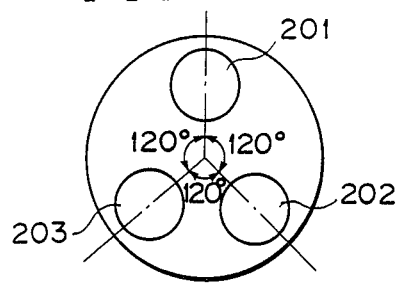
Figure 19:
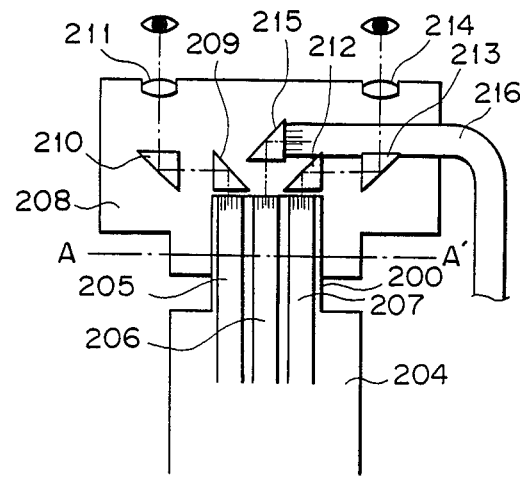

Referring to FIG. 18 in which the front end of the scope is illustrated, the first, second, and the third objective lenses 201, 202, and 203 are respectively disposed at an angular interval of 120° relative to the center of the front end surface of the scope. The light beams converged by the lenses 201, 202, and 203 are imaged on the distal end surfaces of the first, second, and third image guides 205, 206, and 207 so that they are transmitted by the image guides 205, 206, and 207 to the end surface of the scope adjacent to the ocular. Referring to FIG. 19, a fitting portion 200 projected from a scope supporting portion 204 can be arranged to mount an ocular unit 208. When it is mounted, the first, second, and third prisms 209, 215, 212 are disposed corresponding to end surfaces of the first, second, and third image guides 205, 206 and 207. The light beam issued from the end surface of the first image guide 205 is arranged to be made incident upon the first prism 209 at which it is perpendicularly reflected, made incident upon the fourth prism 210, again reflected perpendicularly from the fourth prism 210, and issued outside the ocular unit 208 via the first ocular lens 211. As a result of this, the light beam can be observed by the right eye or the left eye of an observer.

Similarly, the light beam issued from the end surface of the third image guide 207 is arranged to be observed by the right eye or the left eye of an observer via a third prism 212, fifth prism 213, second ocular lens 214, the right eye or the left eye being the other eye of that corresponding to the first ocular lens 211.

The end surface of the second image guide 206 confronts one of the sides of the second prism 215, and the other side of the second prism 215 confronts the issuing end of the light guide 216 which introduces the illuminating light from a light source apparatus (omitted from the illustration) to the ocular unit 208.

Figure 20:
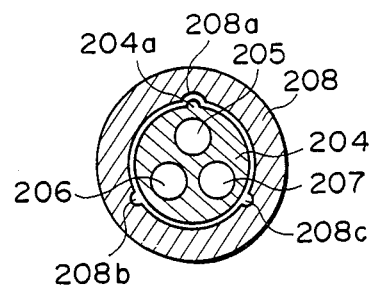

As shown in FIG. 20 which is a cross-sectional view taken along the line A—A' of FIG. 19, the scope supporting portion 204 has a circular cross section, and the portion of the ocular unit 208 which corresponds to the scope supporting portion 204 also has a circular section. As a result of this, the scope supporting portion 204 and the ocular unit 208 are rotatable with respect to each other. Furthermore, the scope supporting portion 204 has a projection 204a, while the ocular unit 208 has a first recess 208a at the position corresponding to the projection 204a. A second and a third recesses 208b and 208c are respectively disposed at an angular interval of 120° with respect to the first recess 208a relative to the center of the scope supporting portion 204.

In the scope supporting portion 204, the first, second, and third image guides 205, 206, and 207 are disposed at an angular interval of 120° similarly to the first, second and third recesses, 208a, 208b, and 208c.

Figure 21:
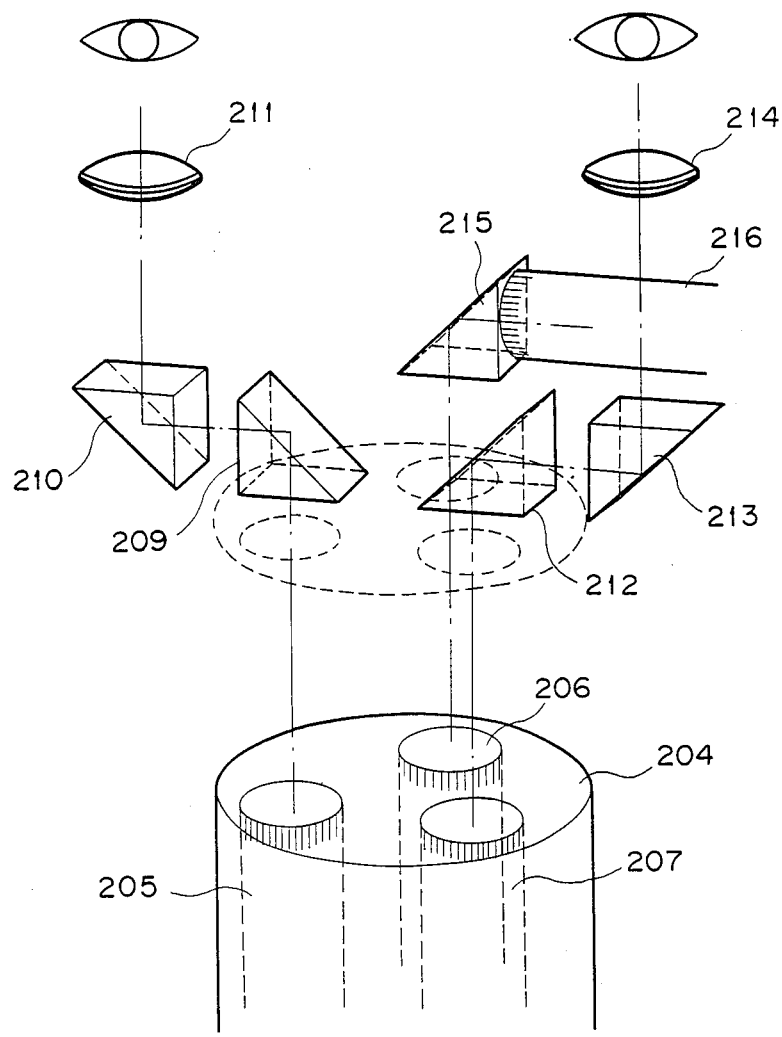

FIG. 21 illustrates the spatial positional relationships between the first, second, and third image guides 205, 206, and 207, the first to fifth prisms 209, 210, 212, 213, 215, the first and second ocular lenses 211 and 214, and the light guide 216.

Referring to FIG. 21, the end surfaces of the first, second, and third image guides 205, 206, 207 are located in such a manner that their end surfaces confronting the ocular unit 208 (omitted from FIG. 21) at the scope supporting portion 204 are disposed at an angular interval of 120° similarly to the illustration in FIG. 20.

As can be clearly seen from this drawing, the first to fifth prisms 209, 210, 212, 213, and 215, the first and second ocular lenses 211 and 214, and the light guide 216 are located at the positions corresponding to the end surfaces of the first, second, and third image guides 205 to 207.

The light is transmitted through the light guide 216 to the ocular unit 208, made incident upon the prism 215 after it has been issued from the end surface of the light guide 216, perpendicularly reflected, and made incident upon the end surface of the second image guide 206. In this state, the second image guide 206 acts as a light guide so as to introduce the illuminating light to the front end of the scope, whereby the illuminating light illuminates the portion to be observed through the objective lens 202.

The image of the portion to be observed is observed by the left eye or the right eye of an observer through the objective lens 201, image guide 205, prisms 209 and 210, and the ocular lens 211. Simultaneously, the image having a parallax from the image observed through the ocular lens 211 is observed by the other eye of the observer through the objective lens 203, image guide 207, prisms 212 and 213, and the ocular lens 214. Therefore, the observer can observe with the right eye and the left eye the stereoscopic images having the parallax each other.

By rotating the unit 208 with respect to the scope supporting portion 204 so as to make the projection 204a which has been confronted the recess 208a confront the recess 208b, the positional relationships are changed wherein the prisms 209, 215, and 212 confront the image guides 205, 206, and 207, respectively. The prism 215 which has confronted the image guide 206 becomes confront the image guide 205. Simultaneously, novel positional relationships are realized in such a manner that the prism 215 which has confronted the image guide 207 confronts the image guide 206 and the prism 209 which has confronted the image guide 205 confronts the image guide 207. As a result of this, the illuminating light is issued through the objective lens 201, and the portion to be observed can be observed with the right and the left eyes through the objective lenses 202 and 203, so that the portion to be observed can be observed stereoscopically. Similarly, when the projection 208a is made confront the recess 208c, the illuminating light is issued through the objective lens 203, an a stereoscopic image can be obtained with the objective lenses 201 and 202.

As described above, according to this embodiment, when the portion to be observed is intended to be stereoscopically observed, three stereo images can be simultaneously obtained by rotating the scope supporting portion 204 and the ocular unit 208 with respect to each other, the three stereo images having the parallax in three directions. Consequently, a further detailed observation can be conducted.

Figure 22:
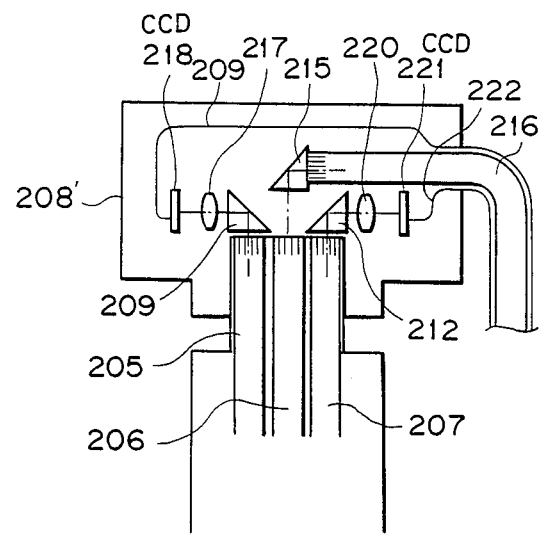
FIG. 22 is a disposition drawing illustrating an essential portion of a modification of a twelfth embodiment.

FIG. 22 illustrates a modified example of an imaging unit 208' which is the modification of the ocular unit 208.

Referring to FIG. 22, a lens 217 upon which the light beam which has been transmitted through the prism 209 is made incident is located at the position at which the prism 210 shown in FIG. 19 is located. A first CCD 218 is disposed at a position at which the image of the portion to be observed is imaged by the lens 217.

Similarly, a lens 220 is disposed at the position at which the prism 212 has been disposed, and a second CCD 221 is located corresponding to the lens 220. Signal cables 219 and 222 which serve as means for transmitting the driving force to and output from the CCDs are respectively connected to the CCDs 218 and 221. The signal cables 219 and 222 are connected to a video processor (omitted from the illustration). According to the structure described above, the stereo image obtained with the naked eye can be obtained in the form of two video images, as a result of this, the image can be observed by a plurality of observers simultaneously.

In this state, a plurality of stereo images having the parallax in the different directions can be obtained. Furthermore, three electric images of the same portion observed from three places, which are not aligned on one straight line and the absolute positional relationships of which are known, can be simultaneously and easily obtained by respectively rotating the scope supporting portion 204 and the imaging unit 208' with the relative positional relationship between them and the portion to be observed which confronts the front end of the scope retained, and recording each image to a certain recording medium (omitted from the illustration). Consequently, a further detailed observation and diagonosis, including the above-described stereoscopic measurement means, can be conducted.

Although, in the above described embodiments and modified examples, the positions of the objective lenses at the front end of the scope are disposed, as shown in FIG. 18, at an angular interval of 120°, this angle is, as can be understood from the above description, not necessary for the present invention to be achieved. For example, minor changes can be, of course, acceptable without deteriorating the effect of the present invention, the minor changes corresponding to, for example, the provision of the water-supply and air-supply channels.

Figure 23:
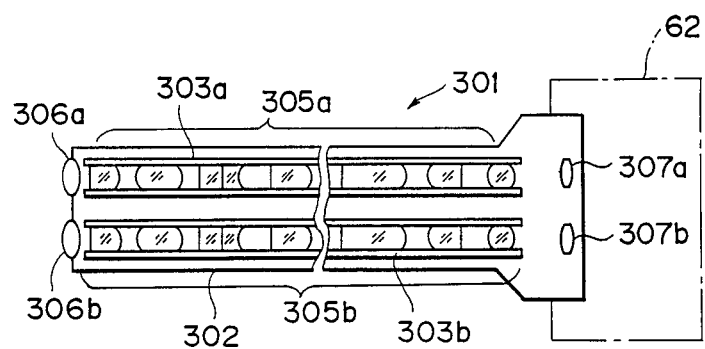
FIG. 23 is a view illustrating the schematic structure of a hard endoscope for realizing stereoscopic observation using a relay optical system according to a thirteenth embodiment of the present invention.

In the above-described fiber scope, a flexible endoscope has been described in which the optical guide or the image guide thereof is made of a fiber bundle, and which thereby has a flexible insertion portion. However, as shown in FIG. 23, a rigid endoscope according to a thirteenth embodiment may be employed.

A rigid endoscope 301 is provided with relay optical systems 305a and 305b comprising: an insertion portion 302 which comprises a rigid cylindrical tube; and two pipes 303a and 303b inserted into this insertion portion 302, the two pipes 303a and 303b being provided with a plurality of lenses disposed successively. The relay optical systems 305a and 305b respectively transmit the images of the objective lenses 306a and 306b to the ocular. The images can be stereoscopically observed with the use of, for example, the ocular unit 62 shown in FIG. 8 through ocular lenses 307a and 307b. Furthermore, a stereo image can be obtained with the use of an imaging unit.

Figure 24:
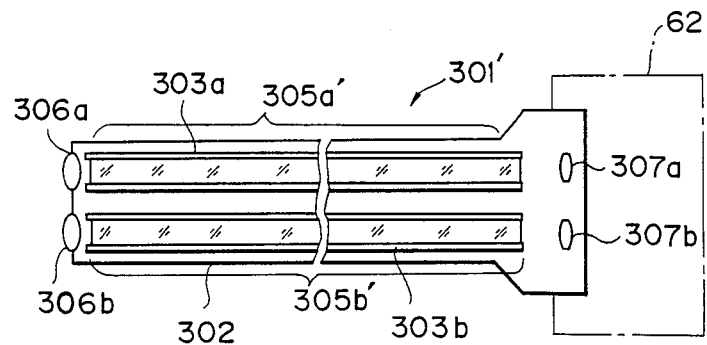
FIG. 24 is a view illustrating the schematic structure of a hard endoscope for realizing stereoscopic observation according to a modification of the thirteenth embodiment.

A rigid endoscope 301' may be, as shown in FIG. 24, employed in which the image guide thereof comprises refractive index gradient type of lenses 305a' and 305b' as an alternative to the relay optical systems 305a and 305b.

Figure 25:
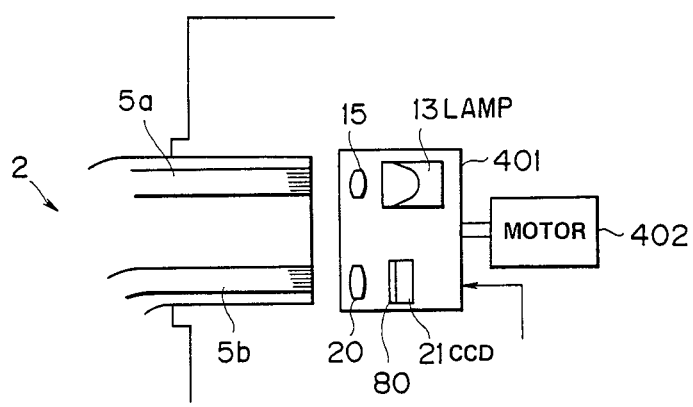
FIG. 25 is a view illustrating an essential portion according to a fourteenth embodiment of the present invention.

FIG. 25 illustrates an essential portion of a fourteenth embodiment of the present invention.

The characteristic of this embodiment lies in that: for example, the endoscope according to the first embodiment is employed, and a rotatable frame 401 to which the imaging lens 20, CCD 22, lamp 13 and lens 15 are fitted is rotated by a motor 402, whereby when the illuminating light is transmitted through the optical guide 5b (or 5a), the other optical guide 5a (or 5b) transmits the optical image, and imaging is performed by a CCD 21.

According to this embodiment, only one illuminating means and one imaging means is necessary and, therefore the stereo image can be economically obtained.

Figure 26:
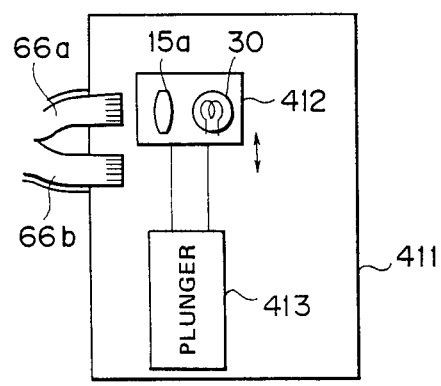
FIG. 26 is a view illustrating the structure of a light source unit according to a fifteenth embodiment of the present invention.

FIG. 26 illustrates a light source unit 411 according to a fifteenth embodiment of the present invention.

According to this light source unit 411, when the illuminating light is supplied to the endoscope 62 shown in FIG. 8, the light guide 31 shown in FIG. 8 is not moved, but a lamp house 412 to which the lamp 30 and lens 15a are fitted is moved by a plunger 413 so that the illuminating light can be alternately supplied to the light guide 66a and 66b.

Figure 27:
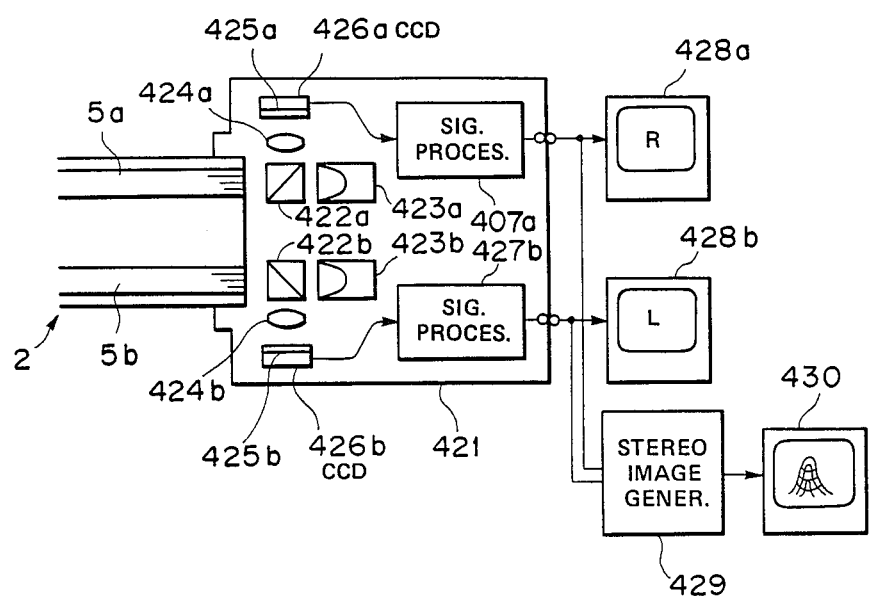
FIG. 27 is a view illustrating the structure of an essential portion according to a sixteenth embodiment.

Although the motor 402 is employed to realize rotation in FIG. 25, a mechanical movable portion is not necessary to obtain the stereo image in the sixteenth embodiment shown in FIG. 27.

For example, beam splitters 422a and 422b confronting the optical guides 5a and 5b are disposed at the connector receiver of a control unit (or a video processer) 421 to which the optical guides 5a and 5b of the endoscope 2 shown in FIG. 1 are fitted. Lamps 423a and 423b are disposed confronting end surfaces of the beam splitters 422a and 422b, while imaging lenses 424a and 424b are disposed confronting the other end surfaces of the same. CCDs 426a and 426b to which color filters 425a and 425b are fitted are provided on the plane at which the focal point is disposed.

The outputs from the CCDs 426a and 426b are supplied to the signal processing apparatus 427a and 427b wherein they are signal-processed, and converted into the NTSC combined image signal or three primary color signals corresponding to red, green and blue. Then, they are displayed by a right-monitor 428a and a left-monitor 428b. Furthermore, they are supplied to a stereo image generating circuit 429, whereby a stereo image can be displayed using the two signals.

The present invention is not limited to an apparatus in which the imaging element such as CCD is used, but it may employ imaging tubes.

Furthermore, infrared rays can make the stereo image to be displayed as an alternative to visible rays red, green and blue.

Furthermore, partial combination of the embodiments is included in the scope of the present invention.

Now, the above mentioned stereo endoscope(s) can be also used as non-stereo (i.e. mono) endoscope(s).

What is claimed is:

1. A stereo endoscope apparatus comprising:
an elongated insertion portion;
first and second optical guide means inserted into said insertion portion, and through which an optical image can be transmitted;
a lens system for imaging said optical image at each front end surface of said first and second optical guides disposed at the front end of said insertion portion;
light output means for outputting illuminating light to the other end surfaces of said first and second optical guides;
imaging means for imaging said optical image transmitted to the other end surfaces of said first and second optical guides; and
illuminating/imaging control means for introducing said optical image transmitted through one of said guide means to said imaging means when said illuminating light output from said light output means is supplied to the other end of said first or second optical guide means.

2. A stereo endoscope apparatus comprising:
an elongated insertion portion;
first and second optical guide means inserted into said insertion portion, and through which an optical image can be transmitted;
a lens system for imaging the optical image at each front end surface of said first and second optical guides disposed at the front end of said insertion portion;
light output means for outputting illuminating light to the other end surfaces of said first and second optical guides;
ocular optical system means for introducing said optical image transmitted to the other end surfaces of said first and second optical guides into two ocular openings for observing said optical image; and
illuminating/observing control means for introducing said optical image transmitted through either of said optical guide means to said ocular opening which corresponds to said optical guide means when said illuminating light is supplied to the other one of said first or second optical guide means.

3. A stereo endoscope apparatus according to claim 1 or 2, wherein said optical guide means comprises a fiber bundle.

4. A stereo endoscope apparatus according to claim 1 or 2, wherein said optical guide means comprises a relay optical system in which a plurality of lenses are longitudinally disposed.

5. A stereo endoscope apparatus according to claim 1 or 2, wherein said optical guide means comprises a refractive index gradient type of lens.

6. A stereo endoscope apparatus according to claim 1 or 2, wherein said light output means comprises a lamp outputting white light.

7. A stereo endoscope apparatus according to claim 1 or 2, wherein said light output means comprises a face-successive light output means for successively outputting light beams of a plurality of wave ranges.

8. A stereo endoscope apparatus according to claim 1 or 2, wherein said light output means is able to selectively output said white light and said face-successive light which successively outputs light beams of a plurality of wave ranges.

9. A stereo endoscope apparatus according to claim 1 or 2, wherein said light output means comprises two light source lamps.

10. A stereo endoscope apparatus according to claim 1 or 2, wherein said light output means comprises a single light source lamp.

11. A stereo endoscope apparatus according to claim 1, wherein said imaging means comprises an imaging optical system and an imaging element.

12. A stereo endoscope apparatus according to claim 1, wherein said imaging means comprises two imaging optical systems and two imaging elements.

13. A stereo endoscope apparatus according to claim 1, wherein said imaging means comprises a single imaging element.

14. A stereo endoscope apparatus according to claim 1, wherein said imaging means comprises an imaging element provided with a color filter.

15. A stereo endoscope apparatus according to claim 1, wherein said imaging means comprises an imaging element having no color filter.

16. A stereo endoscope apparatus according to claim 1, wherein means for branching light is provided between said optical guide means and said imaging means.

17. A stereo endoscope apparatus according to claim 16, wherein an image guide is provided between said means for branching light and said imaging element.

18. A stereo endoscope apparatus according to claim 16, wherein a light guide is provided in such a manner that one front end surface thereof confronts said means for branching light.

19. A stereo endoscope apparatus according to claim 1, wherein said imaging means is detachably provided for said optical guide means.

20. A stereo endoscope apparatus according to claim 1, wherein said imaging means is integrally formed with said optical guide means.

21. A stereo endoscope apparatus according to claim 2, wherein said ocular optical system is integrally formed with said optical guide means.

22. A stereo endoscope apparatus according to claim 2, wherein said ocular optical system is detachably provided for said optical guide means.

23. A stereo endoscope apparatus according to claim 2, wherein means for branching light is provided between said optical guide means and said imaging means.

24. A stereo endoscope apparatus according to claim 2, wherein an image guide is provided between said means for branching light and said ocular optical system.

25. A stereo endoscope apparatus according to claim 1, wherein said imaging means is provided separately from said light output means.

26. A stereo endoscope apparatus according to claim 1, wherein said imaging means is accommodated in one housing together with said light output means.

27. A stereo endoscope system comprising:
an endoscope having an elongated insertion portion, a plurality of optical guide means inserted into said insertion portion through each of which an optical image can be transmitted, and a lens system for imaging an optical image at a first end surface of each said optical guide means at the front end of said insertion portion;
light emitting means for supplying illumination light to the other end of a selected one of any of said optical guide means, said light being output from said first end surface for illuminating a subject;
imaging means for making visible an optical image of the subject transmitted to the other end surface of each said optical guide means other than that illuminating said subject;
illuminating/imaging control means for controlling said light emitting means and introducing said transmitted optical image from said.

28. A stereo endoscope apparatus according to claim 27, wherein said optical guide means comprises three optical guide means.

29. A stereo endoscope apparatus according to claim 28, wherein said optical guide means comprises two optical guide means.

30. A stereo endoscope apparatus according to claim 28, wherein said stereo endoscope apparatus further comprises an ocular unit constituted by:
an ocular optical system which is detachably provided for said endoscope, and which confronts said plurality of optical guide means; and
light guide means disposed confronting one of a plurality of said optical guide means.

31. A stereo endoscope apparatus according to claim 30, wherein said ocular unit further comprises an imaging unit constituted by:
a pair of imaging optical systems which can be fitted to said endoscope, and which confronts a plurality of said optical guide means; and
light guide means which confronts one of a plurality of said optical guide means.

32. A stereo endoscope apparatus according to claim 28, wherein said optical guide means is disposed in the circumferential direction at a uniform angle relative to the center of said insertion portion.

33. A stereo endoscope apparatus according to claim 30, wherein said ocular unit is rotatably provided whereby a pair of said ocular optical system confronting a plurality of said optical guide means and said light guide means confronting one of a plurality of said optical guide means can be replaceable.

34. A stereo endoscope apparatus according to claim 31, wherein said imaging unit is rotatably provided, whereby a pair of said imaging optical system confronting a plurality of said optical guide means and said light guide means confronting one of a plurality of said optical guide means can be replaceable.

35. A stereo endoscope apparatus according to claim 29, wherein said stereo endoscope apparatus further comprises an ocular unit constituted by:
a pair of ocular optical systems which can be fitted to said endoscope, and which can confront said two optical guide means; and
single light guide means which can confront said two optical guide means.

36. A stereo endoscope apparatus according to claim 29, wherein said stereo endoscope apparatus further comprises an ocular unit constituted by:
a pair of imaging optical systems which is able to be fitted to said endoscope, and which can confront said two optical guide means; and
single light guide means which can confront said two optical guide means.

37. A stereo endoscope apparatus according to claim 29, wherein said stereo endoscope apparatus further comprises an ocular unit constituted by:
a pair of means for branching light which is able to be fitted to said endoscope, and which confronts said two optical guides;
a pair of ocular optical systems which confronts one end of said means for branching light; and
a pair of light guide means which confronts the other end of said means for branching light.

38. A stereo endoscope apparatus according to claim 29, wherein said stereo endoscope apparatus further comprises an imaging unit constituted by:
a pair of means for branching light which is able to be fitted to said endoscope, and which confronts said two optical guides;
a pair of imaging optical systems which confronts one end surfaces of a pair of said means for branching light; and a pair of light guide means which confronts the other end surfaces of a pair of said means for branching light.

39. A stereo endoscope apparatus according to claim 38, wherein said imaging unit includes a signal cable extending from said imaging unit.

40. A stereo endoscope apparatus according to claim 38, wherein said imaging unit includes no signal cable extending from said imaging unit.

41. A stereo endoscope system comprising:

an endoscope having an elongated insertion portion, first and second optical guide means inserted into said insertion portion, and through which an optical image can be transmitted, a lens system for imaging the optical image at each front end surface of said first and second optical guides disposed at the front end of said insertion portion;

light output means which can be fitted to one end portions of said first and second optical guides of said endoscope, and which supplies illuminating light to said end portions;

light output means for outputting illuminating light to the other end surfaces of said first and second optical guides;

imaging means for imaging said optical image transmitted to the other end surfaces of said first and second optical guides;

illuminating/imaging control means for introducing said optical image transmitted through one of said optical guide means to said imaging means when said illuminating light output from said light output means is supplied to the other one of said first or second optical guide means;

signal processing means for generating image signals by signal-processing the signals which have been optically converted by said imaging means; and monitor means for color-displaying said image signals output by said signal processing means.

42. A stereo endoscope system according to claim 41, wherein said optical guide comprises a fiber bundle.

43. A stereo endoscope system according to claim 41, wherein said optical guide comprises a relay optical system in which a plurality of lenses are longitudinally disposed.

44. A stereo endoscope system according to claim 41, wherein said optical guide comprises a refractive index gradient type of lens.

45. A stereo endoscope system according to claim 41, wherein said light output means comprises a lamp which issues white light.

46. A stereo endoscope system according to claim 41, wherein said light output means comprises face-successive light output means for outputting light of a plurality of wave ranges.

47. A stereo endoscope system according to claim 41, wherein said light output means comprises two light source lamps.

48. A stereo endoscope system according to claim 41, wherein said light output means comprises a single light source lamp.

49. A stereo endoscope system according to claim 41, wherein said imaging means comprises imaging elements provided with color filters.

50. A stereo endoscope system according to claim 41, wherein said imaging means comprises imaging elements having no color filter.

51. A stereo endoscope system according to claim 41, wherein said imaging means comprises two imaging elements.

52. A stereo endoscope system according to claim 41, wherein said imaging means comprises a single imaging element.

53. A stereo endoscope system according to claim 41, wherein means for branching light is provided between the other end surface of said optical guide means and said imaging element.

54. A stereo endoscope system according to claim 53, wherein an image guide is provided confronting one end surface of said means for branching light.

55. A stereo endoscope system according to claim 54, wherein a light guide is provided confronting the other end surface of said means for branching light.

56. A stereo endoscope system according to claim 41, wherein said imaging means is provided separately from said light output means.

57. A stereo endoscope system according to claim 41, wherein said imaging means is integrally formed with said light output means.

* * * * *